(12) United States Patent
Yuan et al.

(10) Patent No.: US 9,952,217 B2
(45) Date of Patent: Apr. 24, 2018

(54) ANTI-HBC QUANTITATIVE DETECTION METHOD AND USES THEREOF IN MONITORING AND CONTROLLING DISEASE PROGRESSION OF CHRONIC HEPATITIS B PATIENT AND IN PREDICTING THERAPEUTIC EFFECT

(71) Applicants: XIAMEN UNIVERSITY, Xiamen (CN); XIAMEN INNOVAX BIOTECH CO., LTD., Xiamen (CN)

(72) Inventors: Quan Yuan, Xiamen (CN); Liuwei Song, Xiamen (CN); Wenbin Zhou, Xiamen (CN); Zuxing Weng, Xiamen (CN); Feihai Xu, Xiamen (CN); Shengxiang Ge, Xiamen (CN); Jun Zhang, Xiamen (CN); Ningshao Xia, Xiamen (CN)

(73) Assignees: Xiamen Innovax Biotech, Co., LTD., Xiamen (CN); Xiamen University, Xiamen (CN)

( * ) Notice: Subject to any disclaimer, the term of this patent is extended or adjusted under 35 U.S.C. 154(b) by 144 days.

(21) Appl. No.: 14/373,611

(22) PCT Filed: Jan. 17, 2013

(86) PCT No.: PCT/CN2013/070573
§ 371 (c)(1),
(2) Date: Dec. 22, 2014

(87) PCT Pub. No.: WO2013/107355
PCT Pub. Date: Jul. 25, 2013

(65) Prior Publication Data
US 2015/0118674 A1   Apr. 30, 2015

(30) Foreign Application Priority Data
Jan. 21, 2012   (CN) .......................... 2012 1 0019389

(51) Int. Cl.
*G01N 33/576* (2006.01)
*G01N 33/569* (2006.01)

(52) U.S. Cl.
CPC ... *G01N 33/56983* (2013.01); *G01N 33/5762* (2013.01); *G01N 2333/02* (2013.01); *G01N 2469/20* (2013.01); *G01N 2800/52* (2013.01); *G01N 2800/56* (2013.01)

(58) Field of Classification Search
CPC ...... A61K 39/12; A61K 39/292; C07K 14/02; G01N 2333/02; G01N 33/576; G01N 2800/52; G01N 33/5762; Y10S 435/81; Y10S 436/82
See application file for complete search history.

(56) References Cited

U.S. PATENT DOCUMENTS

| | | |
|---|---|---|
| 7,713,532 B2 | 5/2010 | Maki et al. |
| 8,383,333 B2 | 2/2013 | Maki et al. |
| 2006/0166187 A1 | 7/2006 | Maki et al. |
| 2010/0285444 A1 | 11/2010 | Maki et al. |

FOREIGN PATENT DOCUMENTS

| | | |
|---|---|---|
| CN | 1694898 A | 11/2005 |
| CN | 1908666 A | 2/2007 |
| CN | 101545906 A | 9/2009 |
| CN | 101726596 A | 6/2010 |

OTHER PUBLICATIONS

Gunther Virology, 1998, vol. 244, pp. 146-160.*
Zignego et al. Arch. Virol. 1997, vol. 142, pp. 535-544.*
Spronk et al. Journal of Clinical Microbiology, 1991, vol. 29, No. 3, pp. 6111-616.*
Fayol et al. Euro. J. Clin. Chem. Clin. Biochem. 1991, vol. 29, pp. 67-70.*
Zoulim et al. Journal of Clinical Microbiology, 1992, vol. 30, No. 5, pp. 1111-1119.*
Li et al. Clin. Vaccine Immunology, 2010, vol. 17, No. 3, pp. 464-469.*
Nebraska Department of health Human Services, hepatitis prevention program publication on Jan. 2009.*
Brunetto et al., "Monitoring the natural course and response to therapy of chronic hepatitis B with an automated semi-quantitative assay for IgM anti-HBc," Journal of Hepatology, 1993, vol. 19, pp. 431-436.
Colloredo et al., "Semiquantitative assessment of IgM antibody to hepatitis B core antigen and prediction of the severity of chronic hepatitis B," Journal of Viral Hepatitis, 1999, vol. 6, pp. 429-434.
Colloredo Mels et al., "Role of IgM antibody to hepatitis B core antigen in the diagnosis of hepatitis B exacerbations," Archives of Virology, 1993, Supplemental, vol. 8, pp. 203-211.
Galli et al., "What is the Role of Serology for the Study of Chronic Hepatitis B Virus Infection in the Age of Molecular Biology?" Journal of Medical Virology, 2008, vol. 80, pp. 974-979.
Han et al., "The novel use of a routine quantitative system to analyze the activity, content and affinity of an antibody to hepatitis B core antigen," Journal of Clinical Virology, 2011, vol. 52, pp. 295-299.
Supplementary Partial European Search Report, EP Serial No. 13738450.9, dated Jun. 9, 2015, 6 pages.
International Search Report dated Apr. 25, 2013 (PCT/CN2013/070573); ISA/CN.
Rodella, A. et al. "Quantitative analysis of HBsAg, IgM anti-HBc and anti-HBc avidity in acute and chronic hepatitis B", Journal of Clinical Virology, 2006, pp. 206-212, No. 37, Amsterdam, NL—ISSN 1386-6532.
Anonymous, WHO International Standard, First International Standard for anti-Hepatitis B core antigen (Anti-HBc), plasma, human, Instructions for use, Version 2.0, 3 pages, 2013.

(Continued)

*Primary Examiner* — Bao Li
(74) *Attorney, Agent, or Firm* — Banner & Witcoff, Ltd.

(57) ABSTRACT

The present invention relates to a method for quantitative detection of anti-HBc and its use in monitoring disease progression of chronic hepatitis B patients and predicting therapeutic effects. By quantitative detection of antibodies against hepatitis B core protein (Anti-HBc), it is able to monitor disease progression of chronic hepatitis B patients, effectively predict therapeutic effects in chronic hepatitis B patients who accept a therapy against hepatitis B virus (especially, a therapy based on interferon and a therapy based on nucleoside/nucleotide analog anti-HBV drug), and thus guide the patients to reasonably choose drugs.

12 Claims, 8 Drawing Sheets

(56) References Cited

OTHER PUBLICATIONS

Horvat & Tegtmeier, "Hepatitis B and D Viruses," in Hepatitis B and D Viruses. Manual of Clinical Microbiology, Murray et al., eds., ASM Press, pp. 1464-1478, 2003.

Kalus et al., "Validation of the Serological Testing for Anti-HIV-1/2, Anti-HCV, HbsAg, and Anti-HBc from Post-mortem Blood on the Siemens-BEP-III Automatic System," Transfus. Med. Hemother. 38, 365-72, 2011.

Lai et al., "Is anti-hbc IgM a useful clinical test in patients with HbsAg-positive chronic hepatitis or primary hepatocellular carcinoma?" Hepatology 8, 514-17, 1988; abstract.

Lok & Negro, "Hepatitis B and D," in Schiff's Diseases of the Liver, Schiff et al., eds., 11th ed., John Wiley & Sons, Ltd. Chapter 24, pp. 537-581, 2012.

Mast et al., "A Comprehensive Immunization Strategy to Eliminate Transmission of Hepatitis B Virus Infection in the United States. Recommendations of the Advisory Committee on Immunization Practices (ACIP) Part 1: Immunization of Infants, Children, and Adolescents," Morbidity and Mortality Weekly Report, vol. 54, pp. 1-33, 2005.

Chen et al., "Poor response to 18-month lamivudine monotherapy in chronic hepatitis B patients with IgM anti-HBc and acute exacerbation," Alimentary Pharmacology & Therapeutics, Jan. 1, 2006, vol. 23, No. 1, pp. 85-90.

Supplemental European Search Report for EP 13738450, Oct. 1, 2015, 6 pages.

Marinos et al., "Quantitative Assessment of Serum IgM Anti-HBc in the Natural Course and During Interferon Treatment of Chronic Hepatitis B Virus Infection," Hepatology, vol. 19, No. 2, 1994, pp. 303-311.

* cited by examiner

HBc-high group: patients with baseline anti-HBc ≥ 29000 IU/ml
HBc-low group: patients with baseline anti-HBc < 29000 IU/ml

ANTI-HBC QUANTITATIVE DETECTION METHOD AND USES THEREOF IN MONITORING AND CONTROLLING DISEASE PROGRESSION OF CHRONIC HEPATITIS B PATIENT AND IN PREDICTING THERAPEUTIC EFFECT

TECHNICAL FIELD

The present invention relates to detection of Hepatitis B virus (HBV) and clinical diagnosis of viral hepatitis type B, more specifically relates to a method of using quantitative detection of antibodies against hepatitis B core protein (Anti-HBc) for monitoring disease progression of chronic hepatitis B in patients, effectively predicting therapeutic effects in chronic hepatitis B patients who accept a therapy against hepatitis B virus (especially, a therapy based on interferon and a therapy based on nucleoside/nucleotide analogue anti-HBV drug), and thus guiding the patients to reasonably choose drugs.

BACKGROUND ART

Infection of hepatitis B virus, especially chronic infection of hepatitis B virus, is one of the most important public health problems in the world. At present, there are more than 0.35 billion patients with chronic infection of hepatitis B virus in the world. Chronic infection of hepatitis B virus may result in liver diseases such as chronic hepatitis B (CHB), liver cirrhosis (LC) and primary Hepatocellular carcinoma (HCC), and more than 1 million people died each year in the world due to chronic infection of hepatitis B virus and associated diseases caused thereby[1].

At present, drugs for treatment of chronic infection of hepatitis B virus are mainly divided into two groups: interferons (IFNs) and nucleoside/nucleotide analogues (NAs). The former includes normal interferon (IFN) and peginterferon (Peg-IFN, also called as long-acting interferon), which brings about effects of inhibiting HBV and treating CHB primarily by overall enhancing immunocompetence of patients; while the later mainly includes 5 drugs: lamivudine (LMV), adefovir dipivoxil (ADV), Entecavir (ETV), Telbivudine (LdT), and Tenofovir, which inhibit HBV replication by directly inhibiting polymerase activity of HBV. For chronic infection of hepatitis B virus, the final object of using the above drugs for treatment of chronic hepatitis B is to get serological negativity or seroconversion for Hepatitis B surface antigen (HBsAg) (HBsAg loss or HBsAg seroconversion) in patients. However, the above existing drugs have limited potency to achieve HBsAg loss or HBsAg seroconversion, and continuous treatment for several years is usually required. Further, hepatitis B virus E antigen seroconversion (HBeAg seroconversion) is another important event during the procedure of chronic infection of hepatitis B virus, which usually accompanies with remittal and good prognosis of clinical hepatitis, and thus clinical doctors and researchers commonly use "whether HBeAg seroconversion occurs in patients after treatment" as primary indicator for determining whether treatment is effective or not. Besides HBeAg seroconversion, sustained virological response (SVR) is also used as a secondary indicator for determining therapeutic effects of clinical treatment of hepatitis B[2,3].

In view of the end point of therapy that patients with chronic hepatitis B achieve HBeAg seroconversion, there are significant differences in terms of therapeutic effects and drug compliance between IFNs and NAs. IFNs (mainly referring to Peg-IFN or long-acting interferon) have therapeutic effects superior to NAs, 30-50% of HBeAg positive patients could achieve HBeAg seroconversion after one year (52 weeks) treatment with the former, while only 10-30% of HBeAg positive patients could achieve HBeAg seroconversion with the treatment of the later. However, the side-effects of IFNs therapy are usually greater than those of NAs, the subjects usually are accompanied with adverse reaction such as fever, headache, weakness, epilation, leukopenia, and some patients could not stand with these side effects. In contrast, oral drugs of NAs have less side-effects, and good compliance. In term of price, the drug cost for one year treatment with IFNs (mainly referring to Peg-IFN or long-acting interferon) is about 15,000 RMB, while the drug cost for treatment with NAs is usually less than 10,000 RMB. In view of the above differences of the two groups of drugs, it is of fundamental significance to perform effective evaluation and forecasting before treatment of patients and then select an optimized drug for treatment of chronic hepatitis B.

The achievement of HBeAg seroconversion in a patient mainly depends on whether the patient per se has sufficient specific immunocompetence against HBV, or whether the patient could obtain sufficient specific immunocompetence against HBV via drug therapy. Thus, quantitative assay of specific immunocompetence against HBV of a patient with chronic hepatitis B could be used to predict the probability of HBeAg seroconversion occurred in the patient with chronic hepatitis B to be treated. For a long time, serum ALT level of a chronic hepatitis B patient is used as an indirect surrogate marker for evaluation of host immunocompetence against HBV. This is because serum ALT level of chronic hepatitis B patient reflects inflammation/necrosis level of liver cells of the patient, while HBV is immune causative virus, which induces liver inflammation or necrosis of liver cells due to immunological response mediated by anti-HBV T cells, so that there is certain correlation between serum ALT level and host anti-HBV immunocompetence. In general, it is believed that patients with serum ALT level greater than the upper normal limit (ULN) by 2 times usually have better therapeutic effects in anti-HBV treatment (referring to probability of HBeAg seroconversion achieved by treatment) than those without hepatitis reaction, i.e., chronic hepatitis B patients with serum ALT level less than the upper normal limit, while patients with serum ALT level greater than the upper normal limit (ULN) by 5 times usually have better therapeutic effects in anti-HBV treatment than those patients who have hepatitis reaction but have relatively lower ALT level. Nevertheless, the serum ALT level primarily represents degree of liver inflammation, ALT level is not a HBV specific index and may readily affected by other factors (such as accompanied autoimmune hepatitis, alcoholic liver diseases, infection of HCV or other hepatitis viruses), its half-life period is short, and thus it is not very reliable to use ALT level to predict therapeutic effects in treatment of chronic hepatitis B. Besides serum ALT, assay for HBV specific T cell immunologic response (e.g., in vitro stimulation cytokine release test) may also be used for prediction of therapeutic effects in treatment of chronic hepatitis B, but its operation is relatively complicated, its clinic practice and promotion are very difficult, it involves high requirements for test samples (fresh whole blood sample is required), and thus its application prospect is very limited. In sum, there is still not an effective method of evaluation of therapeutic effects before therapy in the art.

Antibodies against hepatitis B core protein (Anti-HBc) are one of most typical serological indicators for HBV infection, and qualitative detection of anti-HBc (determining whether anti-HBc is positive) has been used for more than 35 years in clinic diagnosis of infection of hepatitis B virus. Serum anti-HBc positive result suggests that the subject had been or is being infected with HBV, and this antibody usually continuously exists in serum of HBV infected person for life. At present, the developed methods for detection of anti-HBc antibodies are primarily based on mechanism of competitive or suppressive immunodetection, and these methods can be effectively used for qualitative detection of anti-HBc. However, being restricted with technical mechanism, their detection dynamic linear range is usually narrow (generally within a range of one order of magnitude), and their detection stability is poor and cannot be satisfactorily applied for quantitative detection of anti-HBc. According to the related reviews, there is not an effective method and reagent for quantitative detection of anti-HBc before the publication of the present invention; and the clinical values and corresponding uses of quantitative detection of anti-HBc are unknown so far.

CONTENTS OF THE INVENTION

Since hepatitis B virus core protein has very strong immunogenicity, its serum antibody level indicates capability of humoral immune response (B cell immune response) specifically against HBV in host individual, and reflects whole immunologic competence of host against HBV. To this end, the inventors of the present invention believe that precise detection of serum anti-HBc level of chronic hepatitis B patients could indicate competence of specific immune response against HBV in patients, and can predict final therapeutic effects of treatment with drugs (including interferon drugs, nucleoside/nucleotide analogues) to be accepted by the patients. The present invention relates to a method for precisely quantitative detection of antibody level of anti-HBc in serum/plasma of a patient with infection of hepatitis B virus, and a use of quantitative detection of anti-HBc in monitoring progression of chronic hepatitis B in patients, as well as predicting therapeutic effects of treatment in chronic hepatitis B patients.

Specifically, the present invention relates to an immunological detection method for precisely quantitative detection of serum anti-HBc level, the method being able to be fulfilled by enzyme-linked immunosorbent assay or chemiluminescent detection method.

The method has advantages that the linear dynamic range of a single detection is 1.5 orders of magnitude or more, that is, the upper limit of precise quantitation for single detection is at least 32 times higher than the lower limit of precise quantitation. This feature is a basis for precise quantitative detection of serum anti-HBc level, and is not possessed by the methods for detection of anti-HBc in the prior art before the present invention.

The results obtained by applying the method to samples of patients of different stages of chronic infection of hepatitis B virus and series samples of natural progression of disease course of patients showed that quantitative level of serum anti-HBc is highly correlated to hepatitis activity and host immune state of patients, and the quantitatively measured value of anti-HBc could be used to effectively discriminate whether patients are of stage of immune activation or hepatitis activity. This suggests that clinic use of the method for quantitative detection of anti-HBc as disclosed by the present invention or equivalent methods thereof are conducive to monitoring and determining disease progression of chronic hepatitis B patients.

The results obtained by applying the method to cohort samples of chronic hepatitis patients accepting treatment of adefovir dipivoxil and long-acting interferon showed that basic anti-HBc level was in positive correlation with therapeutic response rate. This suggests that clinic use of the method for quantitative detection of anti-HBc as disclosed by the present invention or equivalent methods thereof can evaluate and predict therapeutic effects before chronic hepatitis B patients accept treatment of drugs such as adefovir dipivoxil, long-acting interferon or those with similar mechanism, and are conducive to guiding the selection of therapeutic drugs and therapeutic time, thereby improving therapeutic efficiency.

On the other hand, the present invention relates to a use of a reagent for quantitative detection of level of antibody against hepatitis B virus core protein in manufacturing a diagnostic agent for monitoring disease progression of chronic hepatitis B patients and/or effectively predicting therapeutic effects before chronic hepatitis B patients accept treatment against hepatitis B virus.

In one specific embodiment, the quantitative detection of antibody against hepatitis B virus core protein is performed by one or more of the following methods: enzyme-linked immunosorbent assay, chemiluminescent immunodetection method, time-resolved fluorescence detection method, immunoturbidimetry method, immunochromatographic method, immuno-percolation method.

In one specific embodiment, single detection of level of antibody against hepatitis B virus core protein has a linear dynamic range of 1.5 orders of magnitude or more, that is, the upper limit of precise quantitation for single detection is 32 times or more higher than the lower limit of precise quantitation.

In one specific embodiment, the quantitative detection of antibody against hepatitis B virus core protein comprises the following steps:

a) providing a hepatitis B virus protein capable of specifically binding an antibody against the hepatitis B virus core protein, the protein can comprise full-length of amino acid sequence of hepatitis B virus core protein (from the $1^{st}$ amino acid to the $183^{th}$ amino acid), or can comprises only an amino acid sequence of primary immune-dominant zone of hepatitis B virus core protein (for example, from the $1^{st}$ amino acid to the $149^{th}$ amino acid), the protein is immobilized on a solid support, acts as a solid phase antigen, and is used for capturing an antibody against hepatitis B virus core protein existing in a serum sample;

b) providing a labeled antigen capable of specifically binding to the antibody against hepatitis B virus core protein that is captured on the solid phase antigen, the labeled antigen can comprise full-length of amino acid sequence of hepatitis B virus core protein (from the $1^{st}$ amino acid to the $183^{th}$ amino acid), or can comprises only an amino acid sequence of primary immune-dominant zone of hepatitis B virus core protein (for example, from the $1^{st}$ amino acid to the $149^{th}$ amino acid), the signal generating substance on the labeled antigen can be horse radish peroxidase, alkaline phosphatase, or acridinium ester;

c) providing quantitation standard samples with known concentrations for drawing a quantitation standard curve, which usually consist of 3-6 samples containing antibody against hepatitis B virus core protein in different concentrations. The unit of concentration can be IU/ml, PEIU/ml, or other units of concentration or titer which source can be traced;

d) contacting the sample (sample to be tested or quantitation standard sample) with the solid phase antigen so that an antibody against hepatitis B virus core protein, if exists, in the sample is captured to form a complex of solid phase antigen-antibody against hepatitis B virus core protein;

e) contacting the labeled antigen with the product of step d), i.e., the complex of solid phase antigen-antibody against hepatitis B virus core protein, so as to form a complex of solid phase antigen-antibody against hepatitis B virus core protein-labeled antigen;

f) contacting a substrate or a solution capable of activating signal generation with the complex of solid phase antigen-antibody against hepatitis B virus core protein-labeled antigen as formed in step e), so as to generate a measurable signal, and measuring the intensity of the generated signal with a corresponding measurement instrument;

g) performing linear regression fit of the measured signals of quantitation standard samples (usually 3-6 samples) with their corresponding concentrations, to obtain a mathematical formula for calculating sample concentration from a measurement signal;

h) introducing the measured signal of sample to be tested into the formula of step g), and calculating the concentration of antibody against hepatitis B virus core protein in the sample to be tested;

i) when the concentration of antibody against hepatitis B virus core protein as calculated in step h) is higher than the upper limit of precise quantitation of the detection method, the sample to be tested is diluted, and steps a) to h) are repeated, until the measured concentration falls in the range between the upper limit and lower limit of precise quantitation of the corresponding detection method. The concentration of antibody against hepatitis B virus core protein contained in the sample to be tested is obtained with calculation of multiplying the measured value after dilution by the dilution ratio.

In one specific embodiment, the diagnostic agent of the present invention is used in chronic hepatitis B patients who accept different therapeutic drugs, the drugs include: long-acting interferon (pegylated interferon, Peginterferon), normal interferon (interferon), lamivudine (LMV), adefovir dipivoxil (ADV), entecavir (ETV), telbivudine (LdT), tenofovir, or other drugs useful in treatment of chronic hepatitis B.

In one specific embodiment, the common criterion for predicting therapeutic effect of a therapy in patients before the therapy is: the therapeutic effect (response rate) obtained by patients with higher level of antibody against hepatitis B virus core protein in serum of patients before the therapy is superior to that of patients with lower level of antibody against hepatitis B virus core protein in serum of patients before the therapy; the criterion of therapeutic effect can be hepatitis B virus E antigen seroconversion (i.e., conversion from HBeAg(+)/anti-HBe(−) to HBeAg(−)/anti-HBe(+) in chronic hepatitis B patients who accept therapy), or can be virology response (i.e., serum HBV DNA load falling to 1000 Copies/ml or less in chronic hepatitis B patients), or other clinical indicators that can indicate remission of disease condition or good prognosis.

In one specific embodiment, the common criterion for monitoring disease progression of chronic hepatitis B patients is: abnormal increase of level of antibody against hepatitis B virus core protein which suggests occurrence of liver inflammation of patients and activation of host immune response specifically against hepatitis B virus.

In one specific embodiment, the present invention relates to a use of anti-HBc in manufacturing a kit for evaluating response in chronic hepatitis B patients who accept therapy of adefovir dipivoxil and pegylated interferon.

In one specific embodiment, the present invention relates to a use of anti-HBc in manufacturing a kit for monitoring disease progression of chronic hepatitis B patients.

In one specific embodiment, the present invention relates to a use of anti-HBc in manufacturing a kit for predicting disease stage of hepatitis B patients.

(A) serum anti-HBc level and ALT level of patients infected with HBV of different stages;

(B) serum HBV DNA level and HBsAg level of patients infected with HBV of different stages;

(C) ROC curve analysis for determining immune activation state of subject based on serum anti-HBc level;

(D) average anti-HBc level of different ALT stratified patients;

(E) correlation analysis of serum anti-HBc level and ALT level.

Notation of acronyms: PBI, patients of before infected; IT, patients in immune tolerance phase; IC, patients in immune clearance phase; LR, patients in low replication phase; ENH, HBeAg negative hepatitis; LC, patients of liver cirrhosis; HCC, patients of primary liver cancer.

Figure 7:
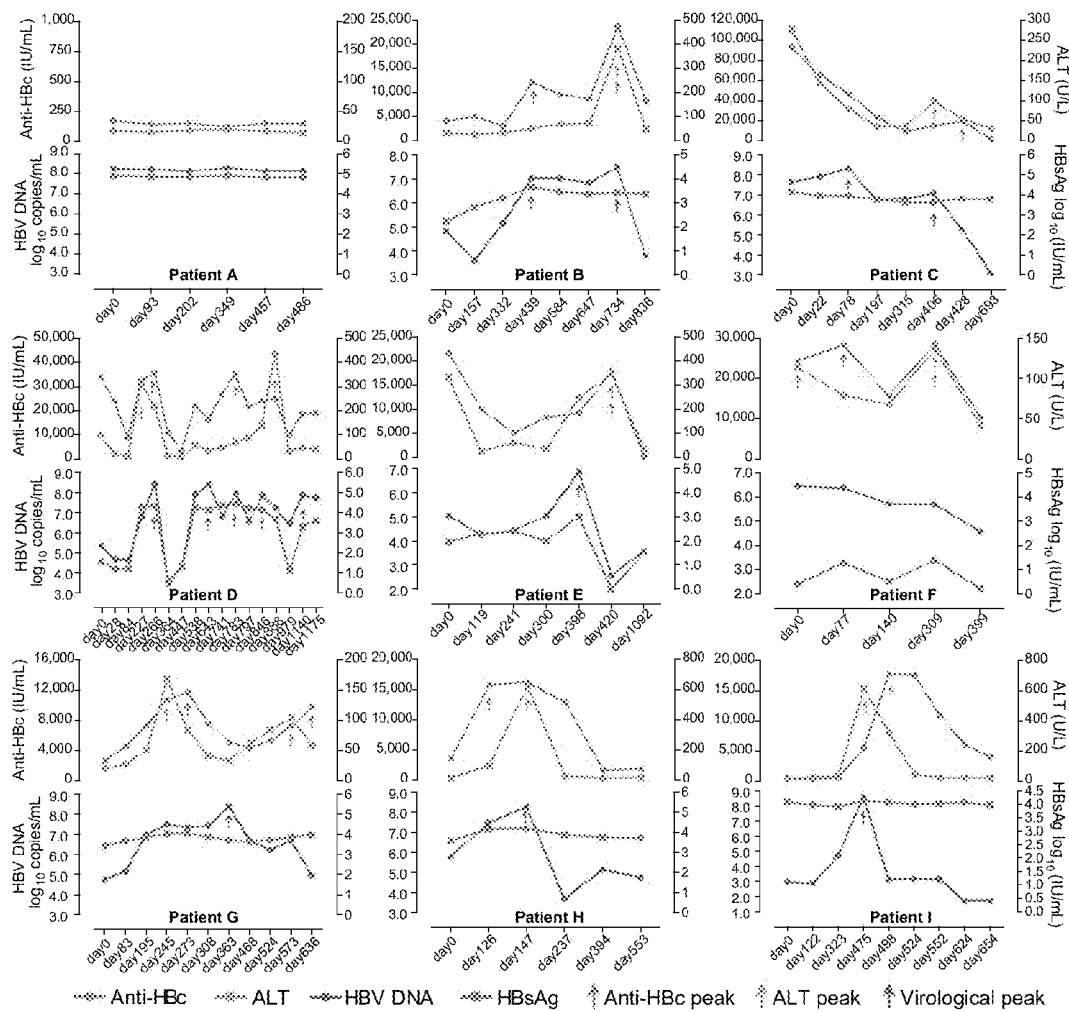

FIG. 7 shows dynamic changes of levels of serum anti-HBc, ALT, HBV DNA and HBsAg during natural progression of chronic hepatitis B virus carriers.

Figure 8:
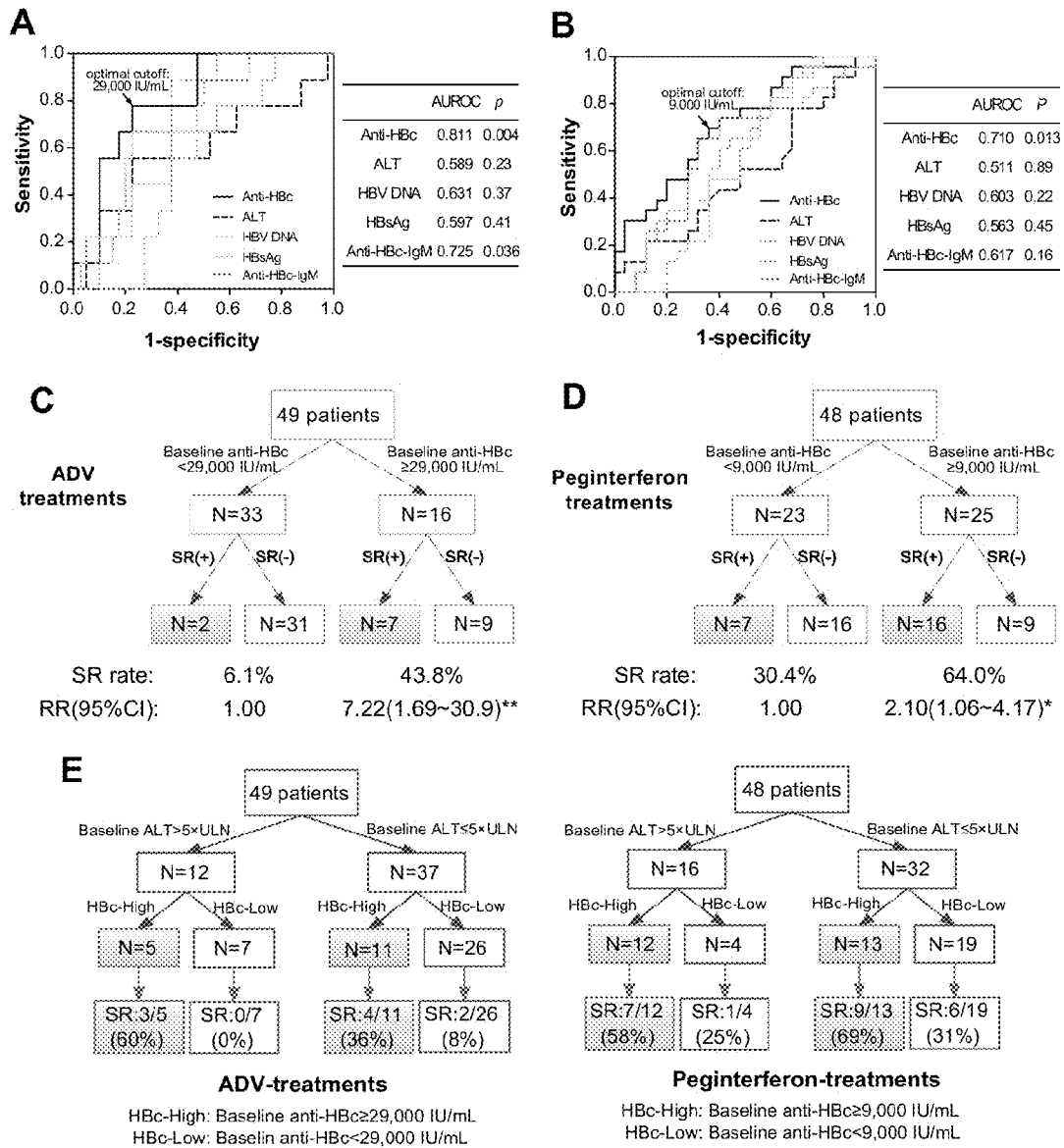
Figure 9:
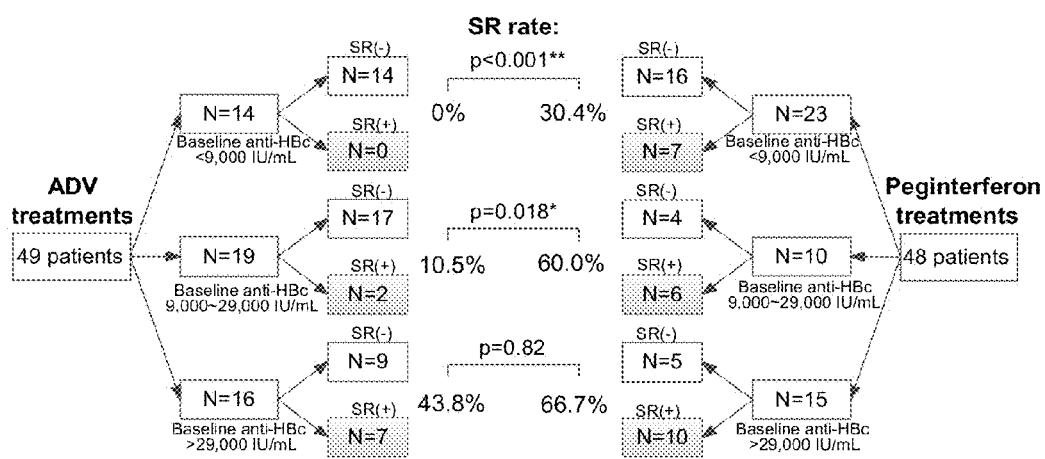
Figure 10:
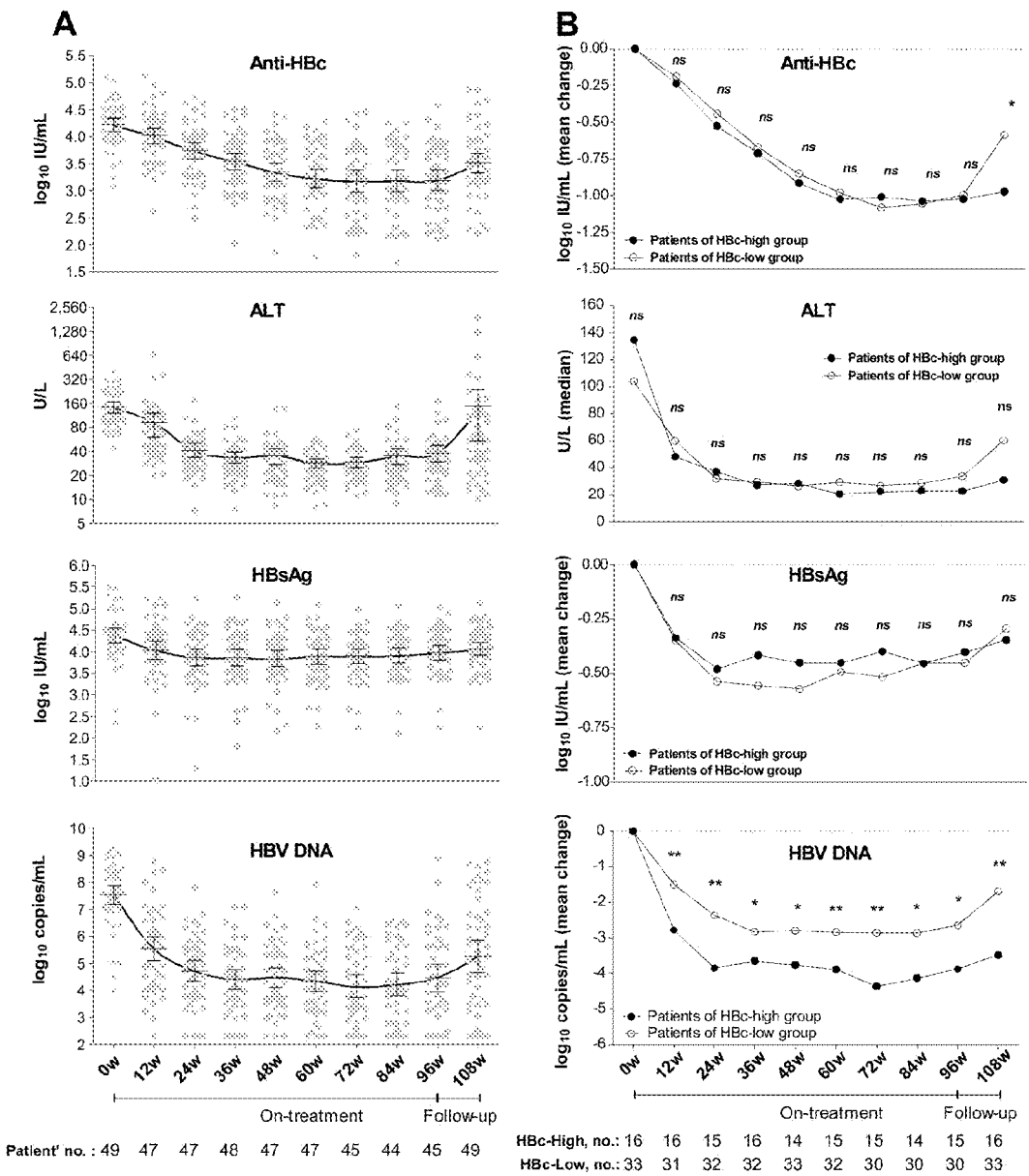

FIG. 8 shows post-treatment HBeAg seroconversion rate as predicted with serum anti-HBc level of chronic hepatitis B patients before therapy:

(A) using anti-HBc level before treatment to predict HBeAg seroconversion of chronic hepatitis B patients after accepting therapy of adefovir dipivoxil;

(B) using anti-HBc level before treatment to predict HBeAg seroconversion of chronic hepatitis B patients after accepting therapy of pegylated interferon;

(C) using serum anti-HBc level to predict HBeAg seroconversion occurrence rate in patients after accepting therapy of adefovir dipivoxil;

(D) using serum anti-HBc level to predict HBeAg seroconversion occurrence rate in patients after accepting therapy of pegylated interferon;

(E) using anti-HBc level before treatment to predict HBeAg seroconversion rate in stratified patients of different baseline ALT levels;

FIG. 9 shows HBeAg seroconversion occurrence rates in stratified patients of different baseline anti-HBc levels after accepting therapy of adefovir dipivoxil and pegylated interferon;

FIG. 10 shows dynamic changes of quantified levels of serum markers in patients during and after therapy of adefovir dipivoxil.

SPECIFIC MODELS FOR CARRYING OUT THE INVENTION

Unless other defined, all technical or scientific terms used in the present text have common meanings known by those skilled in the art associated with the present invention.

In Example 1 of the present invention, an anti-HBc ELISA (enzyme-linked immunosorbent assay, microwell plate method) quantitative detection method was established, this method could precisely determine content of anti-HBc in serum sample, the linear dynamic range for precise quantitation of single detection was up to 1.8 order of magnitude (0.04-2.5 IU/ml), and such a feature was not possessed by the known methods for detection of anti-HBc [4,5].

In Example 2, an anti-HBc CLEIA (chemiluminescent enzyme-linked immune assay, microwell plate method) quantitative detection method was established, this method could precisely determine content of anti-HBc in serum sample, the linear dynamic range for precise quantitation of single detection was up to 2.7 order of magnitude (0.04-20 IU/ml). The linear dynamic range of this method is broader than that of the anti-HBc ELISA quantitative detection method as described in Example 1, so that the number of dilution required for detection of samples with high anti-HBc was remarkably reduced, and efficiency was improved.

In Example 3, an anti-HBc CLIA (direct chemiluminescent immune assay, microparticle method) quantitative detection method was established, this method could precisely determine content of anti-HBc in serum sample, the linear dynamic range for precise quantitation of single detection was up to 3.02 order of magnitude (0.02-20.8 IU/ml). This method significantly broadened linear dynamic range for single detection in comparison with the anti-HBc ELISA quantitative detection method as described in Example 1, so that the number of dilution required for detection of samples with high anti-HBc was remarkably reduced, and efficiency was improved. This method differs from the anti-HBc CLEIA quantitative detection method as described in Example 2 in that single tube for detection is used, and when full automatic equipment was mounted, it could be used for pick-up detection at any time in clinic.

In Example 4, the above anti-HBc quantitative detection method was applied for evaluation of serum anti-HBc level distribution of HBV infected persons of different phases. The evaluation results showed that in chronic hepatitis B virus infected persons, serum anti-HBc level related to hepatitis activity and host immune state of the infected persons. Thus, anti-HBc level could be used for determining whether chronic hepatitis B virus infected persons were in immune activation state or hepatitis active state, diagnostic accuracy (AUROC) was 0.918 (95% CI: 0.888-0.948), and threshold value for determination was 7400 IU/ml. These results showed that the detection results obtained by the anti-HBc quantitative detection method disclosed in the present invention can help clinic doctors to determine disease phase of patient.

In Example 5, the above anti-HBc quantitative detection method was applied to evaluate dynamic changes of anti-HBc level during natural progression of chronic hepatitis B virus infected persons and its relations with other indexes. The evaluation results showed that when chronic hepatitis B virus infected persons had liver inflammation activity, anti-HBc and ALT increased almost at the same time, anti-HBc peak value usually appeared 3-8 weeks later than ALT peak value, but sometimes could appear before or at the same time as the appearance of ALT peak; during recovery phase of hepatitis, ALT returned normal quickly, while anti-HBc returned to baseline level 12-20 weeks later. This result further suggests the anti-HBc level of chronic hepatitis B virus infected persons as measured by the quantitative detection method of the present invention could be used as a complementary index for ALT measurement, which can help clinic doctors to determine whether patients are in hepatitis active phase or have had hepatitis activity within the last 3-4 months.

In Example 6, the anti-HBc quantitative detection method was applied to evaluate response of chronic hepatitis B patients accepting therapy of adefovir dipivoxil and pegylated interferon. The results showed that the anti-HBc level before the therapy in the chronic hepatitis B patients positively correlated to the HBeAg seroconversion rate after the therapy: the patients with high anti-HBc level (29000 IU/ml in the Example) before therapy could achieve desired effects even with adefovir dipivoxil that was cheap and had less side effects but poor therapeutic effects; while for the patients with middle level (9000-29000 IU/ml in the Example) or lower level (<9000 IU/ml in the Example) of anti-HBc before therapy, the therapeutic effects of adefovir dipivoxil were significantly inferior to long-acting interferon that was expensive and had high side effects but was more potent. In patients with high anti-HBc level (29000 IU/ml in the Example) before therapy, the inhibition effect of adefovir dipivoxil against virus replication was significantly superior to that in the patients with low anti-HBc level (<29000 IU/ml) before therapy. This result suggested that using the quantitative detection method of the present invention to measure the anti-HBc level of chronic hepatitis B virus infected persons before they accept therapy could predict the expected therapeutic effects after they accept therapy of adefovir dipivoxil, long-acting interferon or other drugs having similar mechanism, this is conducive to guiding the choice of therapeutic drug and therapeutic time, thereby improving therapeutic efficiency.

The following examples further describe and illustrate the present invention. The examples are intended to illustrate the present invention, and all reagents, chemicals or biological active material concentrations, the used patients and other variants in the examples are merely to exemplify the application of the present invention, rather than to limit the scope of the present invention.

EXAMPLE

1. Dual Antigen Sandwich Assay Anti-HBc Quantitative Enzyme-Linked Immunosorbent Assay (ELISA) Method 1.1 Preparation of Immobilized Antigen and Labeled Antigen In the method, the immobilized antigen and labeled antigen as used were hepatitis B virus core antigen (HBcAg) capable of specifically binding to anti-HBc antibodies in a sample, the antigen could comprise full-length amino acid sequence of HBcAg (Cp183), or could merely comprise an amino acid sequence of primary immune-dominant zone of HBcAg (Cp149). The HBcAg used in the present invention was obtained by recombinant expression with *E. coli* and purification. As to the expression and purification methods for Cp149 recombination antigen, one may refer to the methods disclosed by Adam Zlotnick, et al[6], while as to the expression and purification methods for Cp183 recombination antigen, one may refer to the methods disclosed by An Li, et al[5]. In the present invention, Cp149 recombination antigen was usually used as immobilized antigen, while Cp183 recombination antigen was used as labeled antigen.

1.2 Preparation of Reaction Plate (1.2.1) Cp149 antigen was diluted with 50 mM CB buffer solution pH9.6 ($NaHCO_3/Na_2CO_3$ buffer solution, final concentration was 50 mM, pH value was 9.6), and final concentration was 3 μg/ml.

(1.2.2) 100 μl of coating solution was added to each well of a 96-well ELISA plate, coating at 2-8° C. for 16-24 h, then coating at 37° C. for 2 h.

(1.2.3) PBST washing solution (20 mM PB7.4, 150 mM NaCl, 0.1% Tween 20) was used to perform washing once. Then, 200 μl of blocking solution (pH7.4, 20 mM $Na_2HPO_4$/$NaH_2PO_4$ buffer solution containing 20% of fetal bovine serum and 1% of casein) was added to each well, blocking at 37° C. for 2 h; and discarding the blocking solution. After drying, the plate was placed in aluminum foil bag and stored at 2-8° C. for standby use.

1.3 HRP Labeling of Cp183 Antigen

Improved sodium periodate method was used. Example of labeling 10 mg Cp183 recombination antigen was as follows.

(1.3.1) Cp183 recombination antigen (5 ml) with concentration of 2 mg/l was loaded in a dialysis bag, dialyzed with 50 mM CB buffer solution at 4° C. for 4 h, and dialysis buffer solution was changed once per 2 h during the dialysis.

(1.3.2) 40 mg of HRP was precisely weighed, dissolved in 2 ml of $ddH_2O$, after dissolution, 2 ml of 20 mg/ml $NaIO_4$ solution was added, reacted at room temperature for 30 min; then 40 ul of ethylene glycol was added, reacted at 4° C. for 30 min to obtain a HRP activation solution (10 mg/ml, 4 ml).

(1.3.3) the HRP activation solution obtained in step 1.3.2 was added to a dialysis bag loaded with Cp183 recombination antigen, mixed homogenously and then dialyzed with 50 mM CB buffer solution at 4° C. under dark condition for 6-8 h, and dialysis buffer solution was changed once per 2 h during the dialysis.

(1.3.4) 0.4 ml of $NaBH_4$ solution (5 mg/ml) was prepared, added to the label reaction solution obtained in step 1.3.3, mixed homogeneously, reacted at 4° C. for 2 h under dark condition.

(1.3.5) after step 1.3.4 was completed, the label reaction solution was loaded into a new dialysis bag, and dialyzed with PBS buffer solution at 4° C. for 4 h.

(1.3.6) after step 1.3.5 was completed, purification was performed with Sephacryl S-300 HR chromatography column as produced by GE Company, so as to separate out Cp183-HRP label.

(1.3.7) the Cp183-HRP label as separated and purified in step 1.3.6 was concentrated to 2 mg/ml, then glycerol was added at a volume ratio of 1:1, mixed homogeneously and stored at −20° C. for standby use.

(1.3.8) the Cp183-HRP label obtained in step 1.3.7 was diluted with enzyme label dilution buffer (pH7.4, 20 mM $Na_2HPO_4$/$NaH_2PO_4$ buffer solution containing 20% of fetal bovine serum, 1% of casein, 10% of sucrose, 0.05% of aminopyrine) at a volume ratio of 1/4000 to obtain an enzyme label reaction solution, which was mixed homogeneously and stored at 2-8° C. for standby use.

1.4 Quantitative Standard Samples

The quantitative standard samples for anti-HBc quantitative detection consisted of a series of samples of hepatitis B virus core protein antibody with different concentrations. The unit of concentration could be IU/ml, PEIU/ml, or could be any other units of concentration or titer which source can be traced. In the present invention, common international unit (IU/ml) was used as unit for anti-HBc quantitation, anti-HBc WHO standard sample (Code: 95/522, 50 IU/ampoule) disclosed by NIBSC[7] was diluted serially to reach 40 IU/mL, 20 IU/mL, 10 IU/mL, 5 IU/mL, 2.5 IU/mL, 1.25 IU/mL, 0.625 IU/mL, 0.3125 IU/mL, 0.156 IU/mL, 0.078 IU/mL, 0.039 IU/mL, 0.02 IU/mL, 0.01 IU/mL, i.e., total 13 different concentrations. The substrate solution used for diluting the standard sample could be blood plasma or serum from anti-HBc negative health blood donor, or could be PBS solution containing 20% of fetal bovine serum.

1.5 ELISA Quantitative Detection of Anti-HBc

One serum sample (No.: P1) of chronic hepatitis B patient was provided, and anti-HBc quantitative detection was performed according to the following steps. In view of the fact that chronic hepatitis B patients usually had relatively high level of anti-HBc, the sample was diluted with PBS solution containing 20% of fetal bovine serum to reach 4 dilution rates: 1:500, 1:2500, 1:12500, 1:62500, and then used for quantitative ELISA detection.

(1.5.1) Sample reaction: one coated ELISA plate was provided, 90 μl of sample dilution solution was added to each well, 10 μl of sample or standard sample was also added to each well, shaken and mixed, then incubated and reacted at 37° C. for 30 min.

(1.5.2) Enzyme label reaction: after step 1.5.1 was completed, the ELISA plate was washed with PBST washing solution (20 mM PB7.4, 150 mM NaCl, 0.1% Tween 20) for 5 times, each well was added with 100 μl of the enzyme label reaction solution as obtained in step 1.3.8, incubated and reacted at 37° C. for 30 min.

(1.5.3) Color development reaction: after step 1.5.2 was completed, the ELISA plate was washed with PBST washing solution (20 mM PB7.4, 150 mM NaCl, 0.1% Tween 20) for 5 times, each well was added with 50 μl of TMB color developing agent (provided by Beijing Wantai Biological Pharmacy Co., Ltd.), incubated and reacted at 37° C. for 15 min.

(1.5.4) Stopping reaction and reading value: after step 1.5.3 was completed, each well of the ELISA plate was added with 50 μl of stop solution (provided by Beijing Wantai Biological Pharmacy Co., Ltd.), and $OD_{450/630}$ value of each well was detected with a plate reader.

Figure 1:
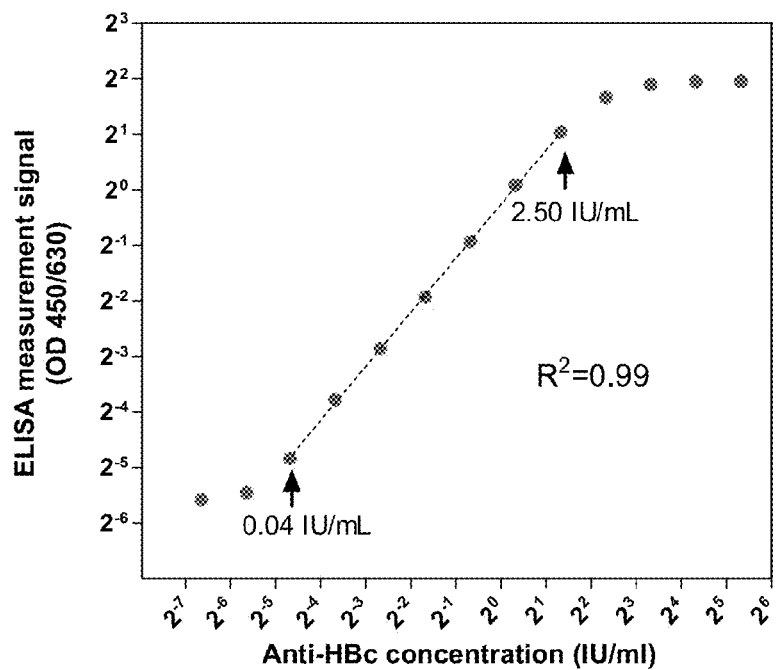
FIG. 1 shows dynamitic linear range of anti-HBc ELISA quantitation method.

(1.5.5) Drawing quantitative standard curve: after step 1.5.4 was completed, the measured values of 13 quantitative standard samples and corresponding concentrations thereof were subjected to linear regression, and the quantitative standard curve of FIG. 1 was drawn. According to FIG. 1, the anti-HBc ELISA method had an upper limit of 2.5 IU/ml and a lower limit of 0.04 IU/ml for precise quantitation, and its linear dynamic range was 1.8 order of magnitude. The formula for calculating anti-HBc concentration from measured $OD_{450/630}$ value was: $Conc._{anti-HBc}$ (IU/mL)=1.2104× $OD_{450/630}$−0.011.

(1.5.6) Obtaining anti-HBc concentration of sample to be tested: the serially diluted samples of P1 serum were subjected to steps 1.5.1 to 1.5.5, then the measured $OD_{450/630}$ value for dilution rate of 1:500 was 3.899; the measured $OD_{450/630}$ value for dilution rate of 1:2500 was 3.801; the measured $OD_{450/630}$ value for dilution rate of 1:12500 was 2.988, the measured $OD_{450/630}$ value for dilution rate of 1:62500 was 0.301; the above measured values were introduced into the formula for calculating anti-HBc concentration as obtained in step 1.5.5, and the concentration value for dilution rate of 1:500 was 4.71 IU/ml, the concentration value for dilution rate of 1:2500 was 4.59 IU/ml, the concentration value for dilution rate of 1:12500 was 3.61 IU/ml, the concentration value for dilution rate of 1:62500 was 0.35 IU/ml. The measured concentration value for dilution rate of 1:62500 was within the linear dynamic range (0.04-2.5 IU/ml) for precise quantitation of ELISA method. Therefore, the original anti-HBc concentration of the sample was 0.35×62500=22083 IU/ml.

Figure 2:
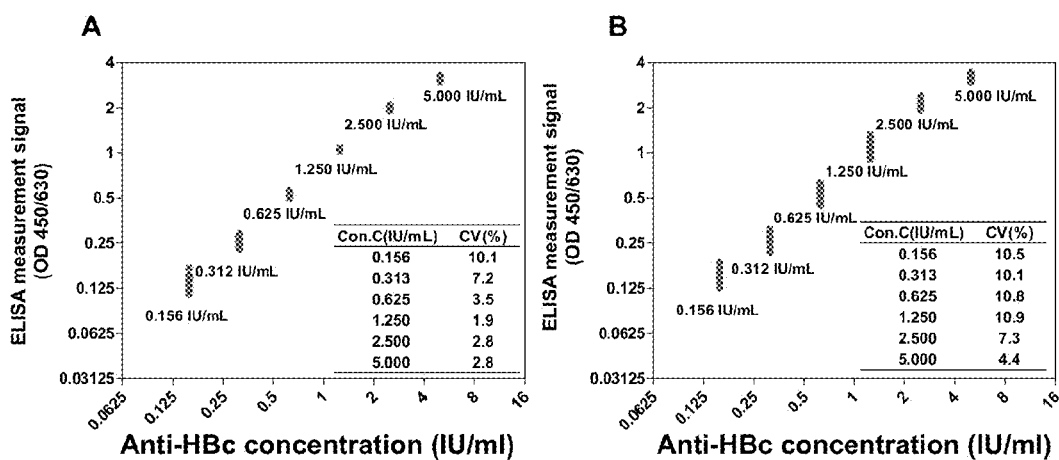
FIG. 2 shows intra-experimental (A) and inter-experimental (B) preciseness of anti-HBc ELISA quantitation method.

(1.5.7) Evaluation of intra-assay preciseness of the detection method: 6 samples with known concentrations were provided, which had anti-HBc quantitated values of 5 IU/ml, 2.5 IU/ml, 1.25 IU/ml, 0.625 IU/ml, 0.3125 IU/ml, 0.156 IU/ml, and in the same test, each of the samples were repeatedly detected in 16 wells according to steps 1.5.1 to 1.5.4, and the intra-assay variable coefficient of measured $OD_{450/630}$ values of each sample was separately calculated after detection, and shown in FIG. 2A, which indicated that the intra-assay variable coefficients of 6 samples were between 2.8% and 10.1%.

(1.5.8) Evaluation of inter-assay preciseness of the detection method: 6 samples with known concentrations were provided, which had anti-HBc quantitated values of 5 IU/ml, 2.5 IU/ml, 1.25 IU/ml, 0.625 IU/ml, 0.3125 IU/ml, 0.156 IU/ml. The above 6 samples were subjected to 16 independent detection tests according to steps 1.5.1 to 1.5.4, after all tests were completed, the inter-assay variable coefficient of measured $OD_{450/630}$ values of each sample was separately calculated, and shown in FIG. 2B, which indicated that the inter-assay variable coefficients of 6 samples were between 4.4% and 10.5%.

Figure 3:
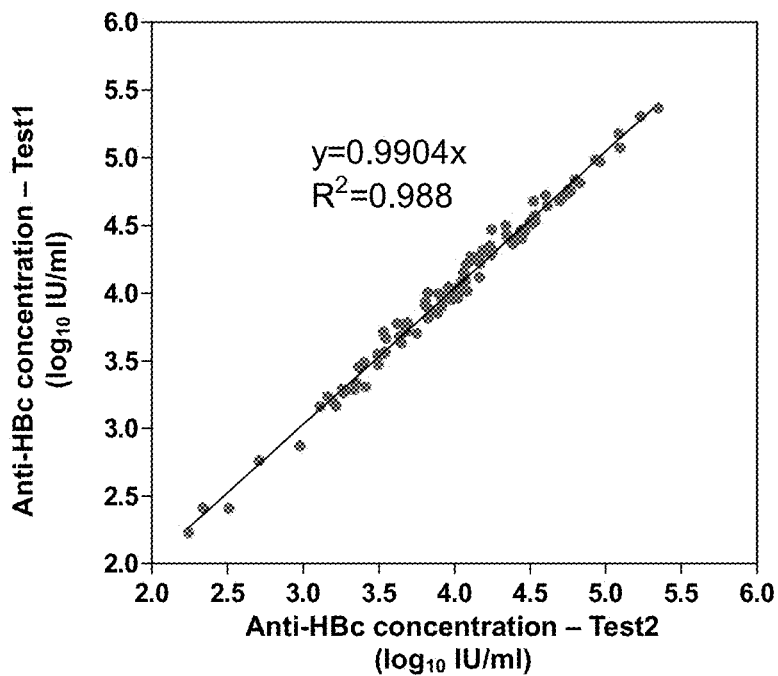
FIG. 3 shows consistency of anti-HBc ELISA quantitation detection results of 104 samples.

(1.5.9) Evaluation of repeatability of the anti-HBc quantitative detection: 104 serum samples of chronic hepatitis B patients (anti-HBc level was between 2.23 $\log_{10}$ IU/ml to 5.37 $\log_{10}$ IU/ml) were randomly selected, and subjected to anti-HBc quantitative detection according to steps 1.5.1 to 1.5.6, the detection was independently repeated for twice, and the results of two detection tests were subjected to regression analysis, and shown in FIG. 3, which indicated that the results of two detection tests were highly consistent, $R^2$=0.988.

2. Dual Antigen Sandwich Assay Anti-HBc Quantitative Chemiluminescent Enzyme-Linked Immunoassay (CLEIA) Method 2.1 Preparation of Immobilized Antigen and Labeled Antigen The method of section 1.1 of Example 1 of the present invention was used to perform the preparation.

2.2 Preparation of Chemiluminescent Reaction Plate

The method of section 1.2 of Example 1 of the present invention was used, with exception that chemiluminescent reaction plate was used as the solid support for the antigen.

2.3 HRP Labeling of Cp183 Antigen

The method and steps of section 1.3 of Example 1 of the present invention were used.

2.4 Quantitation Standard Sample

The quantitative standard samples were the same as those of section 1.4 of Example 1 of the present invention.

2.5 CLEIA Quantitative Detection of Anti-HBc

One serum sample (No.: P1) of chronic hepatitis B patient was provided, and anti-HBc quantitative detection was performed according to the following steps. In view of the fact that chronic hepatitis B patients usually had relatively high level of anti-HBc, the sample was diluted with PBS solution containing 20% of fetal bovine serum to reach 3 dilution rates: 1:500, 1:2500, 1:12500, and then used for quantitative CLEIA detection.

(2.5.1) Sample reaction: one coated chemiluminescent reaction plate was provided, each well was added with 90 μl of sample dilution solution, each wall was then added with 10 μl of sample or standard sample, shaken and mixed homogeneously, then incubated and reacted at 37° C. for 30 min.

(2.5.2) Enzyme label reaction: after step 2.5.1 was completed, the chemiluminescent reaction plate was washed with PBST washing solution (20 mM PB7.4, 150 mM NaCl, 0.1% Tween20) for 5 times, each well was added with 100 μl of the enzyme label reaction solution as prepared in step 1.3.8, incubated and reacted at 37° C. for 30 min.

(2.5.3) Luminescent reaction and measurement: after step 2.5.2 was completed, the chemiluminescent reaction plate was washed with PBST washing solution (20 mM PB7.4, 150 mM NaCl, 0.1% Tween20) for 5 times, each well was added with 100 μl of PICO Chemiluminescent Substrate as manufactured by Pierce Company, and luminescence value (RLU) of each reaction well was immediately read with Orin II chemiluminescent detector.

Figure 4:
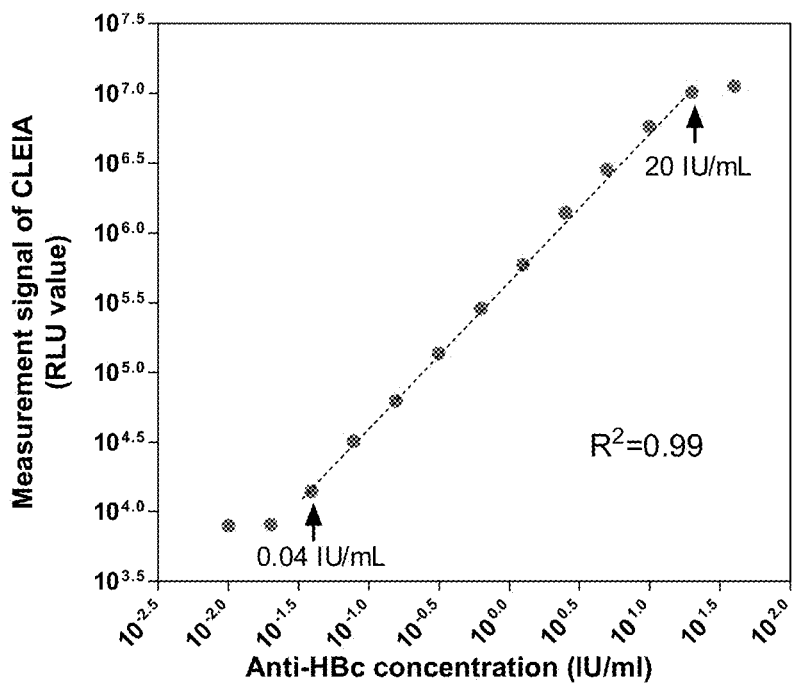
FIG. 4 shows dynamitic linear range of anti-HBc CLEIA quantitation method.

(2.5.4) Drawing quantitative standard curve: after step 2.5.3 was completed, the measured values of 13 quantitative standard samples and corresponding concentrations thereof were subjected to linear regression, and the quantitative standard curve of FIG. 4 was drawn. According to FIG. 4, the anti-HBc CLEIA method had an upper limit of 20 IU/ml and a lower limit of 0.04 IU/ml for precise quantitation, and its linear dynamic range was 2.7 order of magnitude. The formula for calculating anti-HBc concentration from measured RLU value was: Conc.anti-HBc (IU/mL)= $10^{(Log\ 10(RLU) \times 0.9337 - 5.3006)}$.

(2.5.5) Obtaining anti-HBc concentration of sample to be tested: the serially diluted samples of P1 serum were subjected to measurement of steps 2.5.1 to 2.5.4, the measured RLU value for dilution rate of 1:500 was 12115100; the measured RLU value for dilution rate of 1:2500 was 5067890; the measured RLU value for dilution rate of 1:12500 was 889610; the above measured values were introduced into the formula for calculating anti-HBc concentration as obtained in step 2.5.4, and the concentration value for dilution rate of 1:500 was 20.56 IU/ml, the concentration value for dilution rate of 1:2500 was 9.114 IU/ml, the concentration value for dilution rate of 1:12500 was 1.795 IU/ml, wherein the measured values for dilution rates of 1:2500 and 1:12500 were within the linear dynamic range (0.04-20 IU/ml) for precise quantitation of the present CLEIA method. Accordingly, when the measured value for dilution rate of 1:2500 was used for calculation, the original anti-HBc concentration of the sample was 9.114× 2500=22784 IU/ml; while when the measured value for dilution rate of 1:12500 was used for calculation, the original anti-HBc concentration of the sample was 1.795× 12500=22442 IU/ml. The average concentration of the two measured values was 22613 IU/ml, and this concentration value and the concentration value of 22083 IU/ml as measured by ELISA method for the sample had an error of 2.4%, which was in normal variation range.

3. Dual Antigen Sandwich Assay Anti-HBc Quantitative Tubular Microparticle Chemiluminescent Immunoassay (CLIA) Method 3.1 Preparation of Immobilized Antigen and Labeled Antigen The method of section 1.1 of Example 1 of the present invention was used to perform the preparation.

3.2 Preparation of Chemiluminescent Reaction Plate (3.2.1) 1 mg of magnetic beads were provided, washed twice with 1 ml of activation buffer system (50 mM MES 5.0), and supernatant was discarded. 1 mg EDC and 1 mg NHS agent (each was prepared with 50 mM MES 5.0 to reach 10 mg/ml) were added, mixed homogeneously, shaken at room temperature and activated for 20 min.

(3.2.2) the activated magnetic beads was washed twice with 1 ml of activation buffer system (50 mM MES 5.0), and supernatant was discarded. 25 μg of Cp149 antigen was added, mixed homogeneously, shaken at room temperature and reacted for 3 h.

(3.2.3) PBST washing solution (20 mM PB7.4, 150 mM NaCl, 0.1% Tween 20) was used to perform washing for 3 times. Then, each well was added with 2500 μl of preserving solution (20 mM PB7.4, 0.1% BSA, 100 mM Gly, 0.05% TW-20, 0.1% Proclin), and stored at 2-8° C. for standby use.

3.3 Acridinium Ester Labeling of Cp183 Antigen (3.3.1) 50 μg of protein Cp183 was provided, added to 300 μl of label buffer system (50 mM phosphate buffer, pH8.0), added with 8 μl of acridinium ester (5 mM NHS-SAE), and reacted under dark condition at room temperature for 30 min.

(3.3.2) 100 μl of stop buffer solution (phosphate buffer containing 100 mM glycine, pH8.0) was added to the reacted mixture in step (3.3.1), and reacted under dark condition at room temperature for 30 min.

(3.3.3) the labeled protein obtained in step (3.3.2) was loaded in a dialysis bag, dialyzed with dialysis buffer solution (20 mM phosphate buffer solution, pH 7.4) at 4° C. under dark condition for 6-8 h, in which dialysis buffer solution was changed once per 2 hours.

(3.3.4) the labeled protein obtained in step (3.3.3) was transferred to a preserving tube, added with 2% BSA and 50% glycerol, and stored at −20° C. for standby use.

(3.3.5) the Cp183-SAE label obtained in step 3.3.4 was diluted at a volume ratio of 1/500 with acridinium ester label dilution buffer solution (20 mM $Na_2HPO_4/NaH_2PO_4$ buffer solution containing 20% of fetal bovine serum, 1% of casein, 10% of sucrose, 0.05% of aminopyrine, pH7.4) to form a luminescent label reaction solution, which is mixed homogeneously and stored at 2-8° C. for standby use.

3.4 Quantitative Standard Sample

The sample P1 with known concentration of anti-HBc (anti-HBc=22083 IU/ml) was provided, diluted in series manner with PBS solution containing 20% of fetal bovine serum, and separately diluted to reach 4000 IU/mL, 1333 IU/mL, 333 IU/mL, 83.3 IU/mL, 20.8 IU/mL, 5.21 IU/mL, 1.30 IU/mL, 0.33 IU/mL, 0.08 IU/mL, 0.02 IU/mL, 0.005 IU/mL, as quantitative standard samples of CLIA method.

3.5 CLIA Quantitative Detection of Anti-HBc

One serum sample (No.: P2) of chronic hepatitis B patient was provided, and anti-HBc quantitative detection was performed according to the following steps. In view of the fact that chronic hepatitis B patients usually had relatively high level of anti-HBc, the sample was diluted with PBS solution containing 20% of fetal bovine serum to reach 2 dilution rates: 1:500, 1:2500, and then used for quantitative CLIA detection. The P2 sample was subjected to anti-HBc ELISA quantitative detection method of Example 1 and its anti-HBc concentration was determined as 8069 IU/ml.

(3.5.1) Sample reaction: 50 μl of magnetic beads was provided and added to a reaction tube, each well was then added with 10 μl of sample or standard sample, shaken and mixed homogeneously, incubated and reacted at 37° C. for 15 min.

(3.5.2) Luminescent label reaction: after step 3.5.1 was completed, a chemiluminescent reaction plate was washed for 5 times with PBST washing solution (20 mM PB7.4, 150 mM NaCl, 0.1% Tween 20), each well was added with 50 μl of the luminescent label reaction solution as prepared in step 3.3.5, incubated and reacted at 37° C. for 10 min.

(3.5.3) Luminescent reaction and measurement: after step 3.5.2 was completed, the chemiluminescent reaction plate was washed for 5 times with PBST washing solution (20 mM PB7.4, 150 mM NaCl, 0.1% Tween 20), injected in-situ with excitation solution using Sirius-L single tube chemiluminescent detector, and light intensity was detected at the same time.

Figure 5:
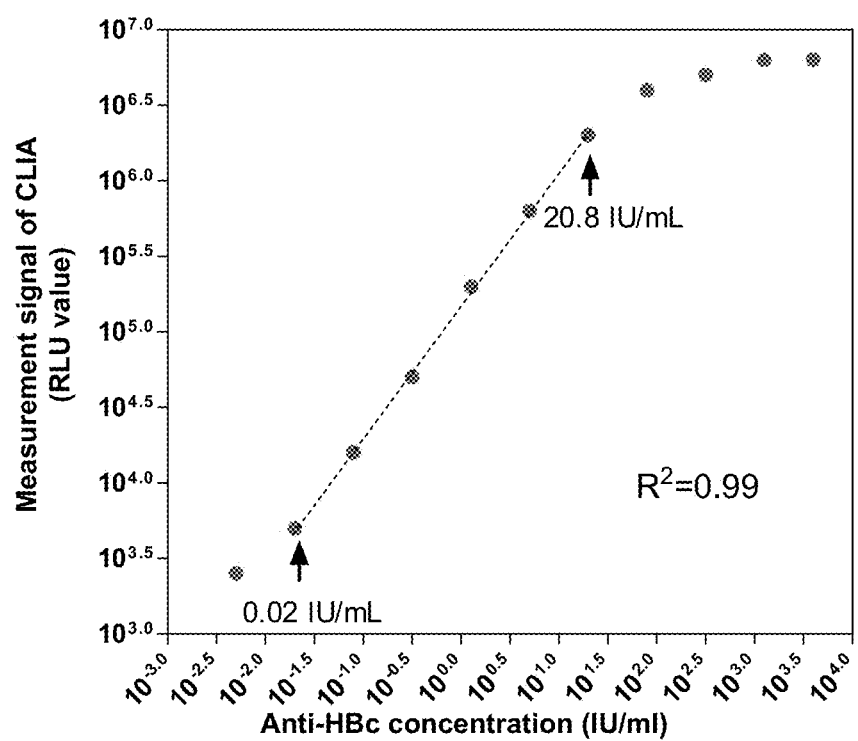
FIG. 5 shows dynamitic linear range of anti-HBc CLIA quantitation method.

(3.5.4) Drawing quantitative standard curve: after step 3.5.3 was completed, the measured values of 11 quantitative standard samples and corresponding concentrations thereof were subjected to linear regression, and the quantitative standard curve of FIG. 5 was drawn. According to FIG. 5, the anti-HBc microparticle chemiluminescent detection (CLIA) method had an upper limit of 20.8 IU/ml and a lower limit of 0.02 IU/ml for precise quantitation, and its linear dynamic range was 3.02 order of magnitude. The formula for calculating anti-HBc concentration from a measured RLU value was: Conc.anti-HBc (IU/mL)= $10^{(Log\ 10(RLU) \times 1.1409 - 5.861)}$.

(3.5.5) Obtaining anti-HBc concentration of sample to be tested: the serially diluted samples of P2 serum were subjected to measurement of steps 3.5.1 to 3.5.4, the measured RLU value for dilution rate of 1:500 was 1571400; the measured RLU value for dilution rate of 1:2500 was 380560; the above measured values were introduced into the formula for calculating anti-HBc concentration as obtained in step 3.5.4, and the concentration value for dilution rate of 1:500 was 16.16 IU/ml, the concentration value for dilution rate of 1:2500 was 3.204 IU/ml, both of which fell into the linear dynamic range (0.02-20.8 IU/ml) for precise quantitation of the CLIA method. Accordingly, when the measured value for dilution rate of 1:500 was used for calculation, the original anti-HBc concentration of the sample was 16.16× 500=8078 IU/ml; while when the measured value for dilution rate of 1:2500 was used for calculation, the original anti-HBc concentration of the sample was 3.204× 2500=8010 IU/ml. The average concentration of the two measured values was 8044 IU/ml, and this concentration value and the concentration value of 8069 IU/ml as measured by ELISA method for the sample had an error of 3.1%, which was in normal variation range.

4. Distribution of Serum Anti-HBc Levels of HBV Infected Persons of Different Phases 4.1 Selection of Cross-Section Patients Serum Samples In the present invention, in order to study the distribution of serum anti-HBc levels of HBV infected persons of different phases, 350 serum samples of health persons who had past HBV infection and healed and 488 serum samples of chronic hepatitis B patients were collected, and all serum samples were stored at −80° C. after serum was separated. Among 488 patients, 109 patients were patients with primary liver cancer, 63 patients were patients with liver cirrhosis, residual 316 patients were patients with simple chronic hepatitis B, and all patients were chosen to exclude possibility of having accompanied infection of hepatitis C virus (HCV), human immunodeficiency virus (HIV), hepatitis D virus (HDV), hepatitis E virus (HEV), and have no clinical medicine evidence of having accompanied autoimmune or metabolic liver diseases.

According to the Guide for Chronic Hepatitis B Clinic Management (2009) of European Association For The Study Of The Liver, the 316 simple chronic hepatitis B patients were divided into different infection phases, in which 52 patients were in immune tolerance phase (IT), who were featured with age of less than 35, HBeAg positive, serum HBV DNA load of greater than $5\times10^7$ copies/ml, ALT level as measured during the past 12 months of always less than the upper limit of normal (ULN, i.e., 40 U/L in the present invention); 104 patients were in immune clearance phase (IC), who were featured with HBeAg positive, serum HBV DNA load of greater than $1\times10^4$ copies/ml, ALT level of greater than 2 times ULN; 75 patients were in low-replicative phase (LR), who were featured with HBeAg negative, serum HBV DNA load of less than $1\times10^4$ copies/ml, ALT level as measured during the past 12 months of always less than ULN; 85 patients were in HBeAg negative hepatitis phase, who were featured with HBeAg negative, serum HBV DNA load of greater than $2\times10^4$ copies/ml, and ALT level of greater than 2 times ULN.

4.2 Clinical Examination Method

Serum ALT level and other liver function biochemical indices of patients were measured 24 h after sample collection; serum HBV DNA load and HBV genotype detection were performed by using methods as reported in prior art documents; HBsAg quantitation was performed by using HBsAg chemiluminescent quantitation kit of Beijing Wantai Biological Pharmacy Co., Ltd.; HBeAg and anti-HBe were measured with Architect chemiluminescent automatic detection system of Abbott Laboratories of US.

4.3 Anit-HBc Quantitation of Serum Samples of Patients

It was performed using the methods of Example 1, Example 2, or Example 3 of the present invention.

4.4 Statistical Method

Comparison of continuous variables among groups was performed using unpaired t-test, or Kruskal-Wallis ANOVA; comparison of classified variables among groups was performed using Mantel-Haenszel $\chi^2$ test or Fisher exact test; and Pearson test was used for correlation analysis. Diagnostic accuracy analysis was performed using receiver operating characteristic (ROC), and diagnostic efficiency was calculated (area under ROC curve, AUROC). P value of less than 0.05 was deemed as having significant statistic difference.

4.4 Basic Features of Patient Cohort

The background data of population statistics, clinical virology and blood biochemistry of the HBV past infected persons and chronic HBV carriers as described in section 4.1 are shown in Table 1.

TABLE 1

Background data of population statistics, clinical virology and blood biochemistry of HBV infected persons of different phases

| | Past HBV | Immune tolerance phase | Immune clearance phase | Low-replicative phase | E antigen negative hepatitis | Hepatitis B cirrhosis | Hepatitis B primary liver cancer |
|---|---|---|---|---|---|---|---|
| | | | | Number of patients: | | | |
| | (n = 350) | (n = 52) | (n = 104) | (n = 75) | (n = 85) | (n = 63) | (n = 109) |
| Age, years, median (range) | 36 (1-59) | 22 (4-35) | 33 (10-65) | 46 (11-75) | 42 (17-82) | 51 (26-77) | 51 (35-77) |
| Gender, males/females | 156/194 | 26/26 | 84/20 | 46/29 | 70/16 | 47/16 | 96/13 |
| Genotype, B/C | — | 36/16 | 71/33 | 34/14 [a] | 56/29 | 24/39 | 52/57 |
| HBeAg-positive, n (%) | 0 | 52 (100) | 103 (100) | 0 | 0 | 20 (32) | 21 (19.2) |
| ALT, U/L, median (range) | 14 (6-40) | 24 (10-39) | 266 (81-3525) | 21 (8-38) | 460 (80-4093) | 56 (11-1831) | 59 (18-1337) |
| ALT-elevation(>40 U/L), n (%) | 0 | 0 | 104 (100) | 0 | 85 (100) | 39 (62) | 80 (73) |
| HBV DNA-positive, % | 0 | 100 | 100 | 100 | 100 | 100 | 100 |
| $Log_{10}$ copies/mL, median (range) | — | 8.6 (7.4-9.6) | 7.2 (3.6-9.6)) | 2.9 (0.3-3.7) | 5.4 (3.1-9.3) | 4.7 (1.0-8.8) | 4.9 (0.4-7.5) |
| HBsAg-positive, % | 0 | 100 | 100 | 100 | 100 | 100 | 100 |
| $Log_{10}$ IU/mL, median (range) | — | 4.7 (3.5-6.0) | 3.9 (0.9-5.7) | 2.8 (0.1-4.2) | 3.6 (−0.3-5.6) | 3.3 (0.8-5.2) | 3.2 (−0.2-3.9) |
| Anti-HBc-positive, % | 100 | 100 | 100 | 100 | 100 | 100 | 100 |
| $Log_{10}$ IU/mL, median (range) | 0.4 (−0.6-2.5) | 3.4 (0.1-4.2) | 4.4 (2.7-5.3) | 3.3 (1.1-4.5) | 4.4 (2.0-5.2) | 4.1 (2.3-5.3) | 4.0 (2.1-5.6) |

Notation:
[a] since HBV DNA load was excessively low, HBV genotypes of 27 patients in low-replicative phase (LR) were not successfully determined.

4.5 Serum Anti-HBc Levels of HBV Infected Persons of Different Phases

Figure 6:
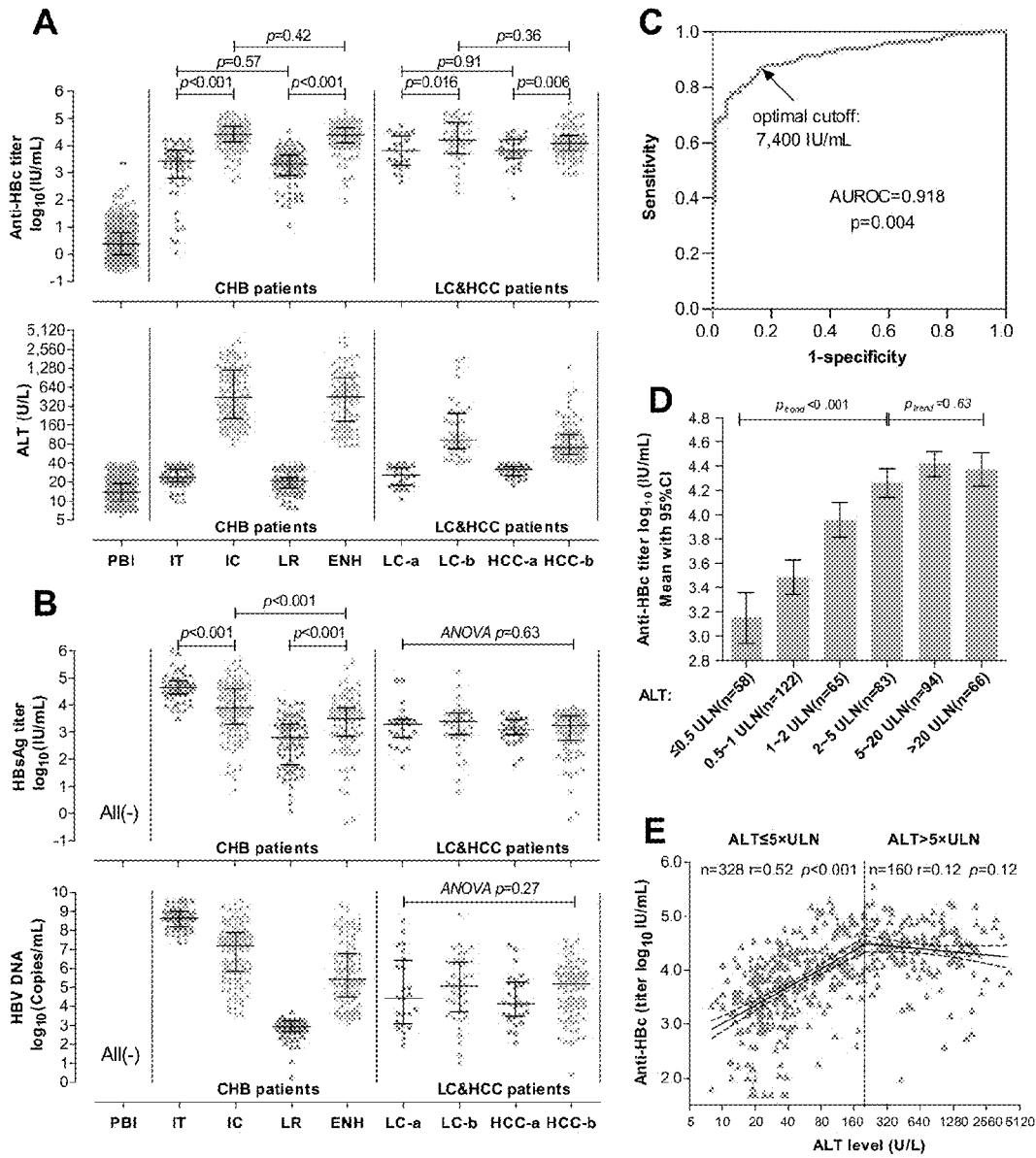
FIG. 6 shows distribution of serum anti-HBc level of patients infected with HBV of different stages.

FIG. 6A/B showed distribution situations of serum anti-HBc level, ALT level, HBsAg level and HBV DNA load of cross-section patients of different disease phases. The past infected persons had serum anti-HBc level significantly lower than that of the chronic HBV carriers (median value: 0.4 vs. 4.1 $log_{10}$ IU/ml, p<0.001, lower more than 1000 times); among simple chronic hepatitis B patients of different infection phases, serum anti-HBc levels were significantly different. The median value of serum anti-HBc level of patients of immune tolerance phase was 3.4 $log_{10}$ IU/ml, the median value of serum anti-HBc level of patients of immune clearance phase was 4.4 $log_{10}$ IU/ml, the median value of serum anti-HBc level of patients of low-replicative phase was 3.3 $log_{10}$ IU/ml, and the median value of serum anti-HBc level of patients of HBeAg negative hepatitis phase was 4.4 $log_{10}$ IU/ml. The analysis of the above data shows that the serum anti-HBc levels of patients of immune clearance phase and HBeAg negative hepatitis phase are significantly higher than those of the patients of immune tolerance phase and low-replicative phase (p<0.001); there is no statistic difference between the serum anti-HBc levels of patients of immune clearance phase and HBeAg negative hepatitis phase (p>0.05), and there is no statistic difference between the serum anti-HBc levels of patients of immune tolerance phase and low-replicative phase, either (p>0.05). The above results show that serum anti-HBc levels of chronic hepatitis B patients are highly correlative to host immune state. High level of anti-HBc indicates that patients are of immune active state of anti-HBV, when anti-HBc level is used for determining whether a subject individual is of immune active state (immune clearance phase or HBeAg negative hepatitis phase), diagnostic efficiency (AUROC, area under curve) is 0.918 (95% confidence interval: 0.888-0.948) via ROC curve analysis (see: FIG. 6C). When the optimized Cutoff value of 7400 IU/ml as calculated using ROC curve is used as the threshold value, diagnostic sensitivity is 87.3%, and diagnostic specificity is 83.5%.

Serum anti-HBc levels of hepatitis B cirrhosis patients and hepatitis B primary liver cancer patients were analyzed and the results are shown in FIG. 6A/B. Among hepatitis B cirrhosis patients, the serum anti-HBc level of 39 patients having ALT≥ULN (LC-b group) was significantly higher than that of 24 patients having ALT<ULN (LC-a group) (median value was: 4.2 $\log_{10}$ vs. 3.8 $\log_{10}$ IU/ml, p=0.016); while among hepatitis B primary liver cancer patients, the serum anti-HBc level of 80 patients having ALT≥ULN (HCC-b group) was significantly higher than that of 29 patients having ALT<ULN (HCC-a group) (median value was: 4.1 $\log_{10}$ vs. 3.8 $\log_{10}$ IU/ml, p=0.006). The above results further confirm the serum anti-HBc level of chronic hepatitis virus infected persons is significantly correlated to ALT level and host immune state.

4.6 Correlation of Anti-HBc Level and ALT Level in Chronic Hepatitis B Virus Carriers The serum anti-HBc levels of different ALT stratified patients among all 488 chronic hepatitis B virus carriers (including simple chronic hepatitis B patients, hepatitis B cirrhosis patients and hepatitis B primary liver cancer patients, n=488) were analyzed, and the results are shown in FIG. 6D. Among patients with ALT≤5×ULN, the average anti-HBc level of patients increased with the increase of ALT level (p trend<0.001); while when ALT reached 5×ULN, the serum anti-HBc level reached the highest value and did not increase further (p trend=0.63). The analysis of correlation shows (FIG. 6E) that in patients with ALT≤5× ULN (n=328), the average serum anti-HBc level was in positive correlation with ALT level (single factor analysis: r=0.52, p<0.001; multiple-factor analysis: R=0.53, p<0.001), but not in correlation with HBV DNA level (p=0.25) or HBsAg level (p=0.33). In patients with ALT≤5× ULN, the quantitative correlation between anti-HBc level and ALT level always exists in either male patients (r=0.53, p<0.001) or female patients (r=0.43, p<0.001); in either patients infected with HBV genotype B (r=0.49, p<0.001) or patients infected with HBV genotype C (r=0.53, p<0.001); in either HBeAg positive patients (r=0.57, p<0.001) or HBeAg negative patients (r=0.50, p<0.001). When ALT>5× ULN (n=160), anti-HBc level has not statistically significant correlation with ALT level (p=0.43), and is not correlative to HBV DNA level (p=0.63) or HBsAg level (p=0.43), either.

5. Dynamic Change of Serum Anti-HBc Level and Relationship Thereof with Other Indicators During Natural Progression of Chronic Hepatitis B Virus Carriers 5.1 Patient Cohort In this Example, a series of serum samples for vertical observation of natural progression from 9 patients in total who did not accept anti-HBV therapy were studied, average observation period was 103±38 weeks (57-168 weeks), follow-up visits was performed for 5-17 times, and 77 serum samples were used.

5.2 Clinical Detection Method

It was performed according to the method described in section 4.2 of Example 4.

5.3 Anti-HBc Quantitation of Serum Samples of Patients

It was performed according to the method described in section 4.3 of Example 4.

5.4 Statistic Methods

Vertical data analysis was performed using generalized estimating equations (GEE), and other statistic methods were performed according to those described in Example 4.

5.5 Dynamic Changes of Serum Markers and Relationship Therebetween During Natural Progression of Chronic Hepatitis B Virus Carriers The dynamic changes of anti-HBc levels, ALT levels, HBsAg levels and serum HBV DNA load of 9 patients (A to G) during follow-up observation period were shown in FIG. 7. Patient A was of immune tolerance phase during follow-up observation period, whose serum HBV DNA load and HBsAg were always at very high levels, while ALT level and anti-HBc level were always at very low levels. Except for Patient A, other patients (B to G) were all subjected to one or more times of hepatitis activation. By observing these patients, it was found that the increase of anti-HBc level was always accompanied with the increase of ALT level, i.e., accompanied with the occurrence of hepatitis. In most situations, when acute attack of hepatitis occurred, the serum anti-HBc level of patients usually reached peak value 3-8 weeks later than ALT level (FIG. 7, for example, the situations of Patient C, first period of Patient D, first period of Patient F, and Patients G and I); in some cases, the serum anti-HBc level of patients could reach peak value earlier or at the same in comparison with ALT level (FIG. 7, for example, the situations of Patient B, Patient D, second period of Patient F and Patient H, Patient E). During recovery phase of hepatitis, the decrease of anti-HBc was slower than ALT, and anti-HBc usually returned to baseline level 12-20 weeks after ALT returned to normal.

In general, multiple-factor vertical data analysis shows serum anti-HBc level are independently correlated with ALT level (β=0.65, p<0.001), but has no statistically significant correlation with serum HBV DNA load (β=−0.006, p=0.98) and HBsAg level (β=−0.034, p=0.45).

6. Anti-Hbc Level can be Used to Predict Therapeutic Effects of Antiviral Therapy in Chronic Hepatitis B Patients 6.1 Patient Cohort Patient cohort A: 49 HBeAg positive patients, all patients accepted therapy of adefovir dipivoxil (10 mg/day), for 96 weeks in total, and were follow-up visited for 12 weeks after stop of therapy.

Patient cohort B: 48 HBeAg positive patients, all patients accepted therapy of peginterferon alpha-2a (long-acting interferon α-2a, 180 μg/week), for 24 weeks in total, and were follow-up visited for 24 weeks after stop of therapy.

The above patients before therapy all met the criteria of disease adaptable for therapy as recommended by the Guide of Clinical Management of Chronic Hepatitis B of APASL: HBsAg was positive for consecutive 1 year or more, HBeAg was positive and anti-HBe was negative, serum ALT level was higher than 2 times of ULN; the patients were chosen to exclude possibility of having accompanied infection of hepatitis C virus (HCV), human immunodeficiency virus (HIV), hepatitis D virus (HDV), hepatitis E virus (HEV), and have no clinical medicine evidence of having accompanied autoimmune or metabolic liver diseases.

6.2 Clinical Detection Method

It was performed according to the method described in section 4.2 of Example 4.

6.3 Anti-HBc Quantitation of Serum Samples of Patients

It was performed according to the method described in section 4.3 of Example 4.

6.4 Definition of Therapeutic End

Main therapeutic end was defined when HBeAg seroconversion occurred at follow-up visit end.

6.5 Statistic Methods.

All statistic methods were performed according to those described in Example 4.

6.6 Basic Features of Patient Cohort

As shown in Table 2.

fective in two cohorts before accepting the therapy were analyzed, and the results were shown in Table 3. For either patients treated with adefovir dipivoxil or patients treated with long-acting interferon, there was no statistically significant difference between patients for whom the therapy was effective and patients for whom the therapy was ineffective in terms of age, gender ratio, ALT level, serum HBV DNA load, HBsAg level and anti-HBc-IgM level. However, the baseline anti-HBc level of patients for whom the therapy was effective was significantly higher than that of patients for whom the therapy was ineffective: in Cohort A, 4.58±0.28 vs. 4.15±0.42 log 10 IU/mL, p=0.005; in Cohort B, 4.32±0.66 vs. 3.81±0.68 log 10 IU/mL, p=0.011. This result suggests that the anti-HBc level before therapy could

TABLE 2

Baseline features of HBeAg positive chronic hepatitis B patients accepting therapy of adefovir dipivoxil (Cohort A) and PEG-interferon (Cohort B)

|  | Cohort A | Cohort B | P value |
|---|---|---|---|
| No | 49 | 48 | — |
| Treatment strategy | ADV 96-week | Pegasys 24-week | — |
| Age, yrs, median (range) | 35 (26~48) | 35 (15~57) | 0.80 |
| Gender, males/females | 44/5 | 35/13 | 0.06 |
| Genotype, B/C | 11/38 | 29/19 | <0.001 |
| ALT strata, >5 × ULN/≤5 × ULN | 12/37 | 16/32 | 0.34 |
| ALT, U/L, median (range)[a] | 110 (44~402) | 168 (32~626) | 0.008 |
| HBV DNA, $\log_{10}$ copies/ml, median (range) | 7.58 (3.97~9.29) | 7.55 (3.44~9.59) | 0.50 |
| HBsAg, $\log_{10}$ IU/ml, median (range) | 4.44 (2.35~5.47) | 4.06 (1.53~5.35) | 0.005 |
| Anti-HBc-IgM, S/CO value, median (range) | 2.10 (0.31~12.7) | 1.78 (0.25~12.2) | 0.45 |
| Anti-HBc, $\log_{10}$ IU/ml, median (range) | 4.29 (3.08~5.11) | 3.98 (2.41~5.36) | 0.15 |

Notation:

[a] all patients were HBeAg positive and had ALT level of greater than 2 × ULN during screening before therapy; when therapy starts, the ALT levels of 11 patients (5 patients of Cohort A, and 6 patients of Cohort B) dropped to 2 × ULN or lower.

ADV: adefovir dipivoxil;

Pegasys: pegylated interferon α-2a;

ULN, upper limit of normal.

6.7 Baseline Anti-HBc Level Correlates to Occurrence Rate of HBeAg Seroconversion after Therapy.

After therapy and follow-up observation, 9 of 49 patients of Cohort A (accepting therapy with adefovir dipivoxil) had occurrence of HBeAg seroconversion at follow-up visit end, therapeutic effective rate was 18.4% (95% CI: 8.8-32.0%); while 23 of 48 patients of Cohort B (accepting therapy of long-acting interferon) had occurrence of HBeAg seroconversion at follow-up visit end, therapeutic effective rate was 47.9% (95% CI: 33.3-62.8%).

The clinical indicators of patients for whom the therapy was effective and patients for whom the therapy was inefpredict expected therapeutic effects of patients. ROC analysis shows that the AUROC value for prediction of HBeAg seroconversion at follow-up visit end using baseline anti-HBc level was 0.810 in Cohort A (95%, CI: 0.675-0.948, p=0.004, see: FIG. 8A), the best cutoff value was 29000 IU/ml, with which the diagnostic sensitivity was 77.8%, the diagnostic specificity was 77.5%; the AUROC value in Cohort B was 0.710 (95% CI: 0.564-0.855, p=0.013, see: FIG. 8B), the best cutoff value was 9000 IU/ml, with which the diagnostic sensitivity was 69.6%, and the diagnostic specificity was 60.0%.

TABLE 3

Analysis of value of baseline features for predication of HBeAg seroconversion after therapy in HBeAg positive chronic hepatitis B patients accepting therapy of adefovir dipivoxil (Cohort A) and therapy of PEG-interferon (Cohort B)

| Characteristics | Cohort A (adefovir dipivoxil) | | | | Cohort B (pegylated interferon α-2a) | | | |
|---|---|---|---|---|---|---|---|---|
| | SR(+) | SR(−) | Univariate p value | Multivariate p value | SR(+) | SR(−) | Univariate p value | Multivariate p value |
| No. | 9 | 40 | — | — | 23 | 25 | — | — |
| Age, yrs | 35 ± 4 | 36 ± 6 | 0.87 | 0.80 | 34 ± 11 | 36 ± 10 | 0.54 | 0.80 |
| Gender, males/females | 7/2 | 37/3 | 0.45 | 0.26 | 17/6 | 18/7 | 0.88 | 0.85 |
| Genotype, B/C | 2/7 | 9/31 | 0.99 | 0.46 | 15/8 | 14/11 | 0.52 | 0.90 |
| ALT strata, >5 × ULN/≤5 × ULN | 3/6 | 9/31 | 0.77 | 0.45 | 8/15 | 8/17 | 0.84 | 0.43 |
| ALT, U/L | 170 ± 88 | 137 ± 79 | 0.28 | 0.29 | 198 ± 129 | 213 ± 149 | 0.71 | 0.26 |
| HBV DNA, $\log_{10}$ copies/mL | 7.03 ± 1.40 | 7.65 ± 1.13 | 0.16 | 0.12 | 7.64 ± 0.92 | 7.04 ± 1.61 | 0.12 | 0.11 |
| HBsAg, $\log_{10}$ IU/mL | 4.32 ± 0.16 | 4.39 ± 0.65 | 0.78 | 0.56 | 4.01 ± 0.42 | 3.92 ± 1.07 | 0.70 | 0.13 |
| Anti-HBc-IgM, S/CO value | 3.13 ± 1.39 | 2.51 ± 2.49 | 0.47 | 0.88 | 3.38 ± 2.85 | 2.72 ± 3.43 | 0.47 | 0.75 |
| Anti-HBc, $\log_{10}$ IU/mL | 4.58 ± 0.28 | 4.15 ± 0.42 | 0.005 | 0.032 | 4.32 ± 0.66 | 3.81 ± 0.68 | 0.011 | 0.026 |

Notation:
Age, ALT level, HBV DNA load, HBsAg level, IgM-Anti-HBc and Anti-HBc level were expressed as Mean ± SD; SR: HbeAg seroconversion.

6.8 Prediction of Occurrence Rate of HBeAg Seroconversion after Therapy Using Baseline Anti-HBc Level The cutoff value as calculated in section 6.7 could be used before therapy to predict occurrence rate of HBeAg seroconversion after patients accept therapy. In Cohort A, as shown in FIG. 8C, 7 of 16 patients with baseline anti-HBc level of greater than 29000 IU/ml had occurrence of HBeAg seroconversion at follow-up visit end (effective rate: 43.8%), while only 2 of 33 patients with baseline anti-HBc level of less than 29000 IU/ml had occurrence of HBeAg seroconversion at follow-up visit end (effective rate: 6.1%), the ratio of occurrence rates (Risk Ratio, RR) of HBeAg seroconversion between high and low anti-HBc groups was 7.22 (95% CI: 1.69-30.9, p=0.006). In Cohort B, as shown in FIG. 8D, 16 of 25 patients with baseline anti-HBc level of greater than 9000 IU/ml had occurrence of HBeAg seroconversion at follow-up visit end (effective rate: 64.0%), while only 7 of 23 patients with baseline anti-HBc level of less than 9000 IU/ml had occurrence of HBeAg seroconversion at follow-up visit end (effective rate: 30.4%), the ratio of occurrence rates (Risk Ratio, RR) of HBeAg seroconversion between high and low anti-HBc groups was 2.10 (95% CI: 1.06-4.17, p=0.006).

The effects of baseline anti-HBc for prediction of HBeAg seroconversion after therapy in patients with different ALT levels were further analyzed, and the results were shown in FIG. 8E. In two cohorts, as for subgroups of patients with baseline ALT level of either ≤5×ULN or >5×ULN, the patients with higher anti-HBc level had higher occurrence rate of seroconversion after therapy in comparison with the patients with lower anti-HBc level. The patients accepting therapy of adefovir dipivoxil and long-acting interferon were combined for analysis, and all patients were divided into 3 groups: high anti-HBc level (≥29000 IU/ml), middle anti-HBc level (9000-29000 IU/ml) and low anti-HBc level (<9000 IU/ml), and the HBeAg seroconversion rates of patients of the 3 groups after therapy were analyzed, and the results were shown in FIG. 9. Among patients with baseline anti-HBc level of ≥29000 IU/ml, 9 of 16 patients accepting therapy of adefovir dipivoxil had HBeAg seroconversion after therapy, the response rate was 43.8%, while this rate in 15 patients accepting therapy of long-acting interferon was 66.7% (10/15), there was not statistically significant difference between them (p=0.82); as for patients with baseline anti-HBc level of 9000-29000 IU/ml, only 2 of 19 patients accepting therapy of adefovir dipivoxil had HBeAg seroconversion after therapy, the response rate was 10.5%, while this rate in 10 patients accepting therapy of long-acting interferon was 60.0% (6/10), there was statistically significant difference between them (p=0.018); as for patients with baseline anti-HBc level of <9000 IU/ml, none of 16 patients accepting therapy of adefovir dipivoxil had HBeAg seroconversion after therapy, while 7 of 23 patients accepting therapy of long-acting interferon had HBeAg seroconversion (30.4%), there was statistically significant difference between them (p<0.001).

6.9 Dynamic Changes of Anti-HBc Level of Patients During and after Therapy of Adefovir Dipivoxil According to dynamic changes of anti-HBc level of patients during and after therapy of adefovir dipivoxil (see: FIG. 10A), the whole therapy and observation period could be divided into 3 phases: (1) baseline to 60 weeks after beginning of therapy, in this phase, the average serum anti-HBc level of patients presented a linear decline with the continuation of therapy (r=0.99, p<0.001), declining 0.20±0.05 $\log_{10}$ IU/mL per 12 weeks; (2) 60 weeks after beginning of therapy to therapy end (96 weeks), the average serum anti-HBc level of patients reached a platform, not declining with the continuation of therapy (p=0.87); (3) after therapy of drug (108 weeks), the average serum anti-HBc level of patients presented a significant bounce in comparison with that at therapy end (96 weeks), average increase being 0.29 $\log_{10}$ IU/ml (p<0.001). In general, the anti-HBc level decreased slower than ALT level, HBV DNA level and HBsAg level during therapy procedure, the former reached platform phase 60 weeks after beginning of therapy, while the later 3 indicators reached platform phase 24 weeks after beginning of therapy. Multiple-factor vertical analysis showed anti-HBc level independently correlated to ALT level (β=0.830, p<0.001), but had no statistically significant correlation with HBV DNA level (β=0.003, p=0.94) or HBsAg level (β=−0.061, p=0.52).

According to the clinical cutoff values determined in section 6.7 of the present Example, all patients accepting therapy of adefovir dipivoxil were divided into 2 groups: ≥29000 IU/ml (n=16, HBc-High) and <29000 IU/ml (n=33, HBc-Low), the dynamic changes of serum anti-HBc, HBV DNA, ALT and HBsAg levels during and after therapy between the two groups were compared, and the results were shown in FIG. 10B. There was no statistic difference between HBc-High and HBc-Low groups in terms of HBV DNA level (7.61±1.15 vs. 7.50±1.22 $\log_{10}$ copies/mL, p=0.77) and HBsAg level (4.34±0.31 vs. 4.38±0.69 $\log_{10}$ IU/mL, p=0.83); while the baseline ALT level of HBc-High group was higher than that of HBc-Low group, but without statistically significant difference. During therapy, the decline curves of ALT level and anti-HBc level of two groups showed no significant difference either in analysis of each of monitoring points or in vertical analysis; however, after therapy of drug, the anti-HBc of HBc-Low group had a remarkable bounce in comparison with that of HBc-High group (p=0.039), and ALT level was in a similar situation, but without statistical significance (p=0.09). As for HBV DNA level, the patients of HBc-High group had serum HBV DNA level significantly lower than that of HBc-Low group (p<0.05) either during or after therapy (except baseline). At follow-up end, the average HBV DNA level of the patients of HBc-High group was decreased by 3.48±2.24 $\log_{10}$ copies/mL in comparison with that before therapy; while the average HBV DNA level of the patients of HBc-Low group was decreased by 1.69±2.05 $\log_{10}$ copies/mL (p=0.008) in comparison with that before therapy. The HBsAg level alterations of the two groups showed no significant difference.

REFERENCES

[1] Dienstag J L. Hepatitis B virus infection. N Engl J Med 2008; 359:1486-1500.
[2] Liaw Y F, Chu C M. Hepatitis B virus infection. Lancet 2009; 373:582-592.
[3] Kwon H, Lok A S. Hepatitis B therapy. Nat Rev Gastroenterol Hepatol 2011; 8:275-284.
[4] Deng L J, Xu Y, Huang J. Developing a double-antigen sandwich ELISA for effective detection of human hepatitis B core antibody. Comp Immunol Microbiol Infect Dis 2008; 31:515-526.
[5] Li A, Yuan Q, Huang Z, Fan J, Guo R, Lou B, et al. Novel double-antigen sandwich immunoassay for human hepatitis B core antibody. Clin Vaccine Immunol 2010; 17:464-469.
[6] Zlotnick A, Johnson J M, Wingfield P W, Stahl S J, Endres D. A theoretical model successfully identifies features of hepatitis B virus capsid assembly. Biochemistry 1999; 38:14644-14652.
[7] WHO International Standard: First International Standard for anti-Hepatitis B core antigen. 10 Nov. 2008 [cited; Available from: www.nibsc.ac.uk/documents/ifu/95-522.pdf

The invention claimed is:

1. A method for treatment of a chronic hepatitis B patient, comprising:
    (a) quantitative detection of the level of total antibodies against hepatitis B virus core protein (HBc) in a serum sample of the chronic hepatitis B patient before the chronic hepatitis B patient accepts a drug against hepatitis B virus; and
    (b1) administering a nucleoside or nucleotide analog to the chronic hepatitis B patient if the level of total antibodies against HBc is higher than 29000 IU/mL; or
    (b2) administering an interferon to the chronic hepatitis B patient if the level of total antibodies against HBc is lower than 29000 IU/mL.

2. The method of claim 1, wherein the quantitative detection of the total antibodies against HBc is performed by a method selected from the group consisting of an enzyme-linked immunosorbent assay, a chemiluminescent immuno-detection method, a time-resolved fluorescence detection method, an immunoturbidimetry method, an immunochromatographic method, and an immuno-percolation method.

3. The method of claim 1, wherein single detection of level of the total antibodies against HBc has a linear dynamic range of 1.5 order of magnitude or more.

4. The method of claim 1, wherein the quantitative detection of the level of total antibodies against HBc comprises the following steps:
    a) providing a solid phase antigen capable of specifically binding an antibody against HBc, wherein the solid phase antigen comprises the primary immune-dominant zone of HBc, wherein the solid phase antigen is immobilized on a solid support and captures antibodies against HBc existing in a serum sample;
    b) providing a labeled antigen capable of specifically binding to antibodies against the HBc captured by the solid phase antigen, wherein the labeled antigen comprises the primary immune-dominant zone of HBc;
    c) providing quantitation standard samples with known concentrations of antibodies against HBc;
    d) contacting:
        (1) a test sample with the solid phase antigen, thereby forming first complexes of the solid phase antigen with antibodies against HBc present in the serum sample; and
        (2) the quantitation standard samples with the solid phase antigen, thereby forming second complexes of the solid phase antigen with antibodies against hepatitis B virus core protein present in the quantitation standard samples;
    e) contacting the labeled antigen with the first and second complexes formed in step d), thereby forming third complexes of the labeled antigen with the first complexes and fourth complexes of the labeled antigen with the second complexes;
    f) contacting a substrate or a solution capable of activating signal generation with the complexes formed in step e), thereby generating a measurable signal, and measuring the intensity of the generated signal with a corresponding measurement instrument;
    g) performing a linear regression fit of the measured signals of quantitation standard samples with their corresponding concentrations to obtain a mathematical formula for calculating sample concentration from a measurement signal;
    h) introducing the measured signal of test sample into the formula of step g), and calculating the concentration of antibodies against the HBc in the test sample;
    i) if the concentration of the total antibodies against HBc as calculated in step h) is higher than the upper limit of precise quantitation of the detection method, the sample to be tested is diluted, repeating steps a) to h) until the measured concentration falls in the range between the upper limit and lower limit of precise quantitation of the corresponding detection method, and the concentration of antibodies against HBc contained in the test sample is obtained with calculation of multiplying the measured value after dilution by the dilution ratio.

5. The method of claim 1, wherein the nucleoside or nucleotide analog is selected from the group consisting of lamivudine (LMV), adefovir dipivoxil (ADV), entecavir (ETV), telbivudine (LdT), and tenofovir.

6. The method of claim 4, wherein the solid phase antigen in step a) comprises the 1st amino acid to the 183th amino acid or the 1st amino acid to the 149th amino acid of HBc.

7. The method of claim 4, wherein the labeled antigen in step b) comprises the 1st amino acid to the 183th amino acid or the 1st amino acid to the 149th amino acid of HBc.

8. The method of claim 3, wherein the upper limit of precise quantitation for single detection is 32 times or more higher than the lower limit of precise quantitation.

9. The method of claim 4, wherein the labeled antigen comprises horseradish peroxidase, alkaline phosphatase, or acridinium ester.

10. The method of claim 5, wherein the nucleoside or nucleotide analog is adefovir dipivoxil (ADV).

11. The method of claim 1, wherein the interferon is long-acting interferon.

12. The method of claim 11, wherein the long-acting interferon is pegylated interferon (Peginterferon).

\* \* \* \* \*